United States Patent
Sanai et al.

(10) Patent No.: US 9,492,688 B2
(45) Date of Patent: Nov. 15, 2016

(54) ULTRASONIC TREATMENT INSTRUMENT USING ULTRASONIC VIBRATIONS

(71) Applicant: OLYMPUS CORPORATION, Tokyo (JP)

(72) Inventors: Hideo Sanai, Hachioji (JP); Yuji Hirai, Ebina (JP)

(73) Assignee: OLYMPUS CORPORATION, Tokyo (JP)

( * ) Notice: Subject to any disclaimer, the term of this patent is extended or adjusted under 35 U.S.C. 154(b) by 71 days.

(21) Appl. No.: 14/470,055

(22) Filed: Aug. 27, 2014

(65) Prior Publication Data

US 2015/0051516 A1   Feb. 19, 2015

Related U.S. Application Data

(63) Continuation of application No. PCT/JP2013/067857, filed on Jun. 28, 2013.

(60) Provisional application No. 61/668,141, filed on Jul. 5, 2012.

(51) Int. Cl.
   *A61N 7/00* (2006.01)
   *A61B 17/32* (2006.01)
   *A61B 17/00* (2006.01)

(52) U.S. Cl.
   CPC ......... *A61N 7/00* (2013.01); *A61B 17/320092* (2013.01); *A61B 2017/0046* (2013.01); *A61B 2017/00411* (2013.01);
   (Continued)

(58) Field of Classification Search
   CPC ................ A61B 17/320068; A61B 2017/320072–2017/320088; A61B 17/320092; A61B 2017/320096
   See application file for complete search history.

(56) References Cited

U.S. PATENT DOCUMENTS

| | | | |
|---|---|---|---|
| 6,004,335 A * | 12/1999 | Vaitekunas | A61B 17/07207 227/180.1 |
| 2006/0265035 A1 | 11/2006 | Yachi et al. | |
| 2009/0088667 A1 | 4/2009 | Masuda | |
| 2009/0275864 A1 * | 11/2009 | Hirai | A61B 17/22004 601/2 |
| 2010/0185197 A1 * | 7/2010 | Sakao | A61B 18/085 606/51 |
| 2011/0015631 A1 | 1/2011 | Wiener et al. | |
| 2011/0172689 A1 | 7/2011 | Smith et al. | |

FOREIGN PATENT DOCUMENTS

| | | |
|---|---|---|
| JP | Y-3-24171 | 5/1991 |
| JP | 2006-341066 A | 12/2006 |

(Continued)

OTHER PUBLICATIONS

Jan. 6, 2015 International Preliminary Report on Patentability issued in International Application No. PCT/JP2013/067857.

(Continued)

*Primary Examiner* — Serkan Akar
(74) *Attorney, Agent, or Firm* — Oliff PLC

(57) ABSTRACT

In a treatment instrument, a load force center of a load force, which is a sum of gravity acting on the treatment instrument and an external force caused by a connected cable, is positioned between two support members of a handle section, and a location of introduction of the cable is disposed in a manner to extend therebetween. In the treatment instrument, an ultrasonic vibration element unit is attached and rotatably coupled to a handle unit, a power receiving section or a power supply section at the coupling constitutes a rotary electrode structure by a cylindrical electrode and a terminal electrode, and power from an outside is received and transmitted between the handle unit and the ultrasonic vibration element unit.

10 Claims, 15 Drawing Sheets

(52) U.S. Cl.
CPC ... *A61B 2217/005* (2013.01); *A61B 2217/007* (2013.01); *A61N 2007/0017* (2013.01)

(56) References Cited

FOREIGN PATENT DOCUMENTS

| JP | 2009-082710 A | 4/2009 |
|----|---------------|--------|
| JP | A-2010-162216 | 7/2010 |
| WO | 2004/112844 A2 | 12/2004 |

OTHER PUBLICATIONS

International Search Report issued in International Patent Application No. PCT/JP2013/067857 dated Jul. 30, 2013 (with translation).
Jan. 6, 2015 Office Action issued in Japanese Patent Application No. 2014-523716.
Feb. 11, 2016 Extended European Search Report issued in European Patent Application No. 13813868.0.

* cited by examiner

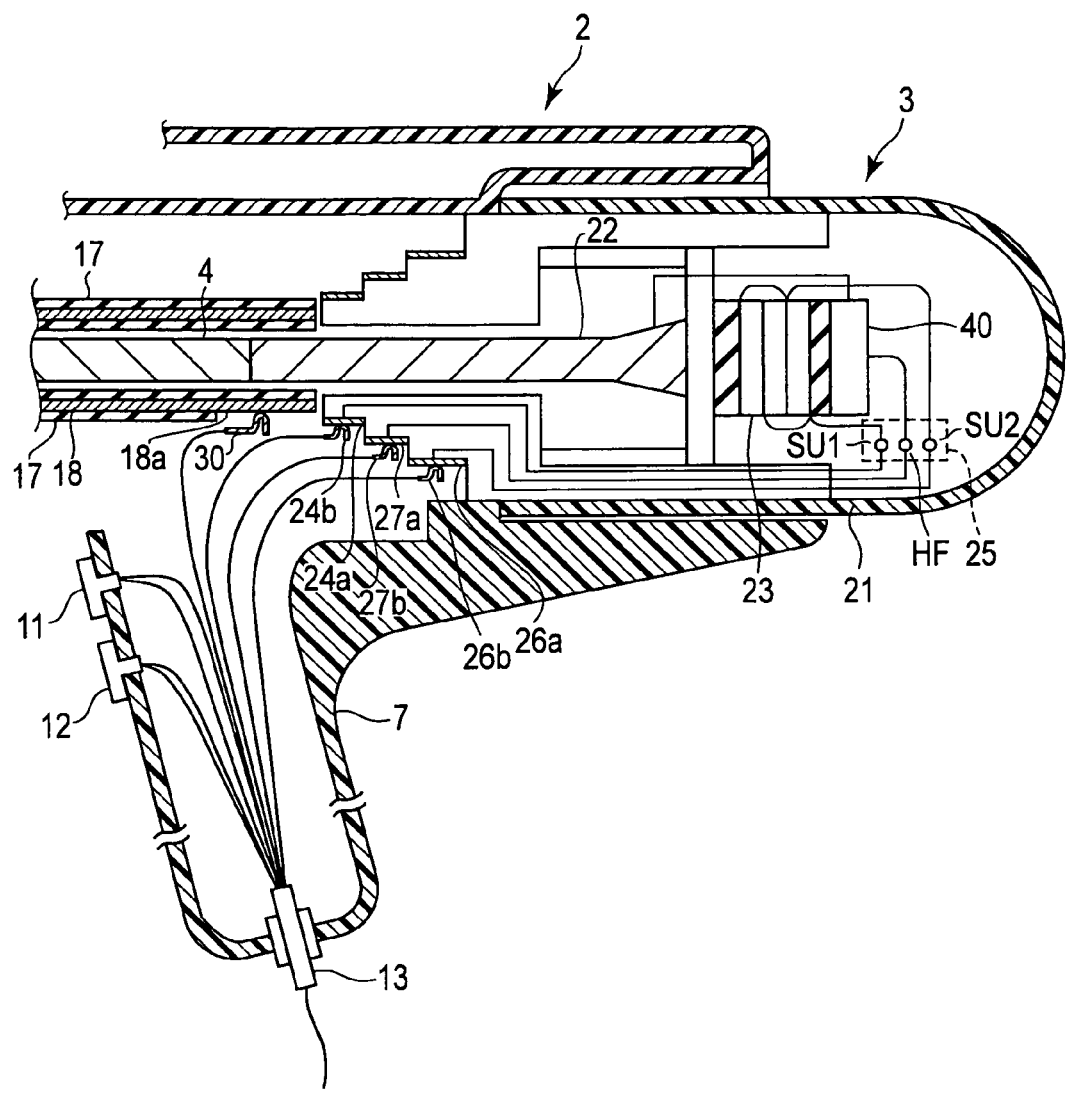
F I G. 3

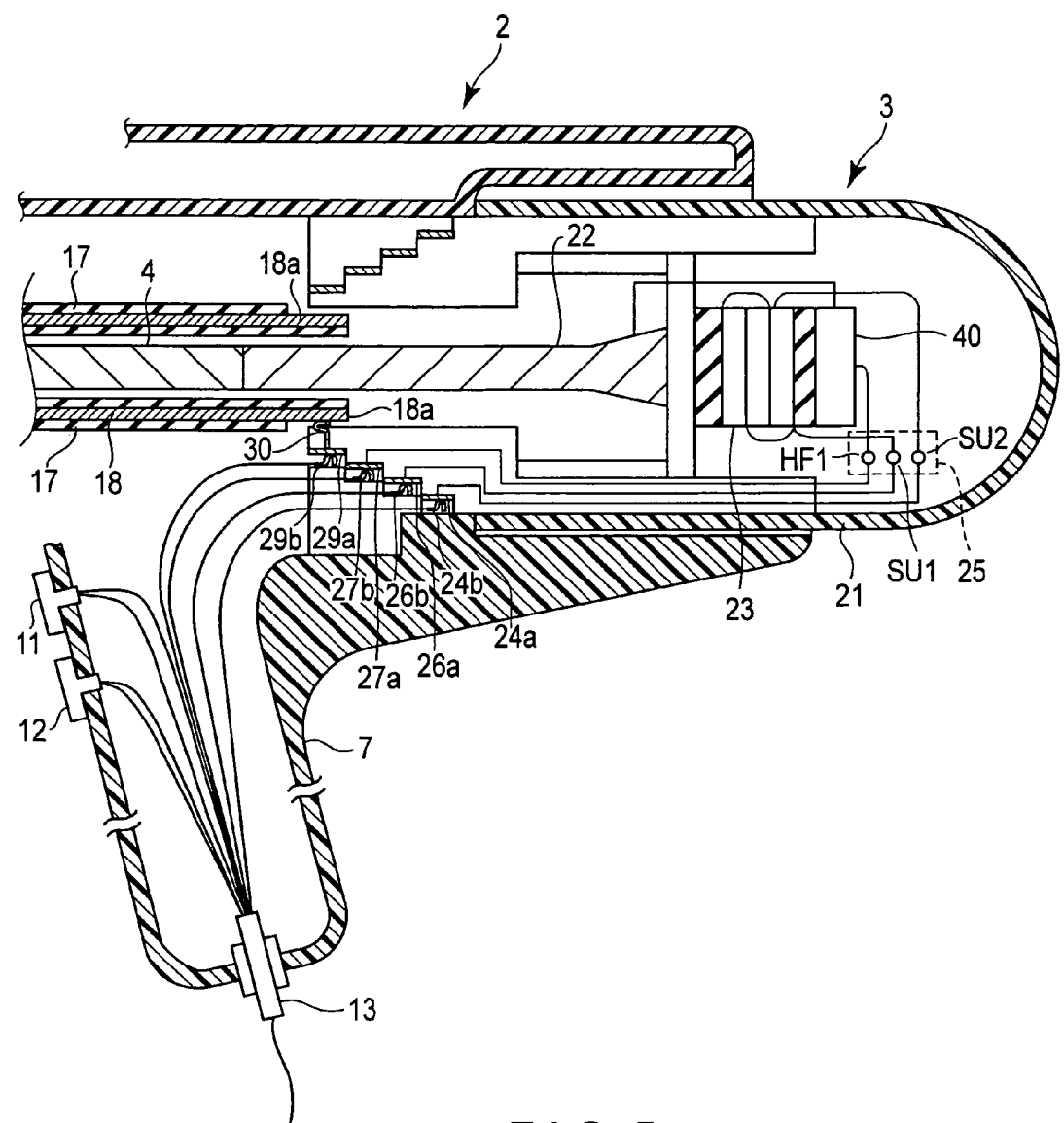
F I G. 5

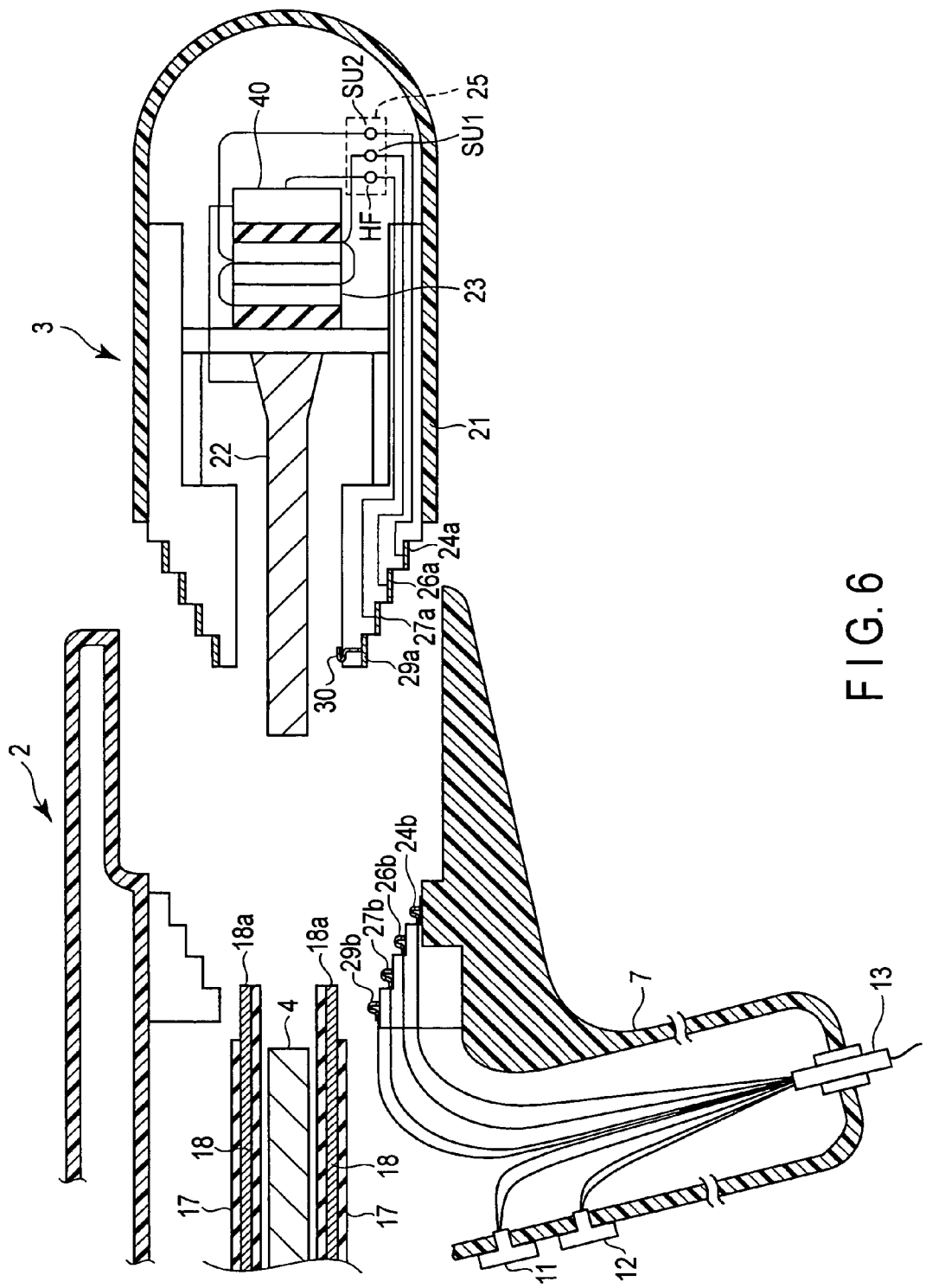
F I G. 6

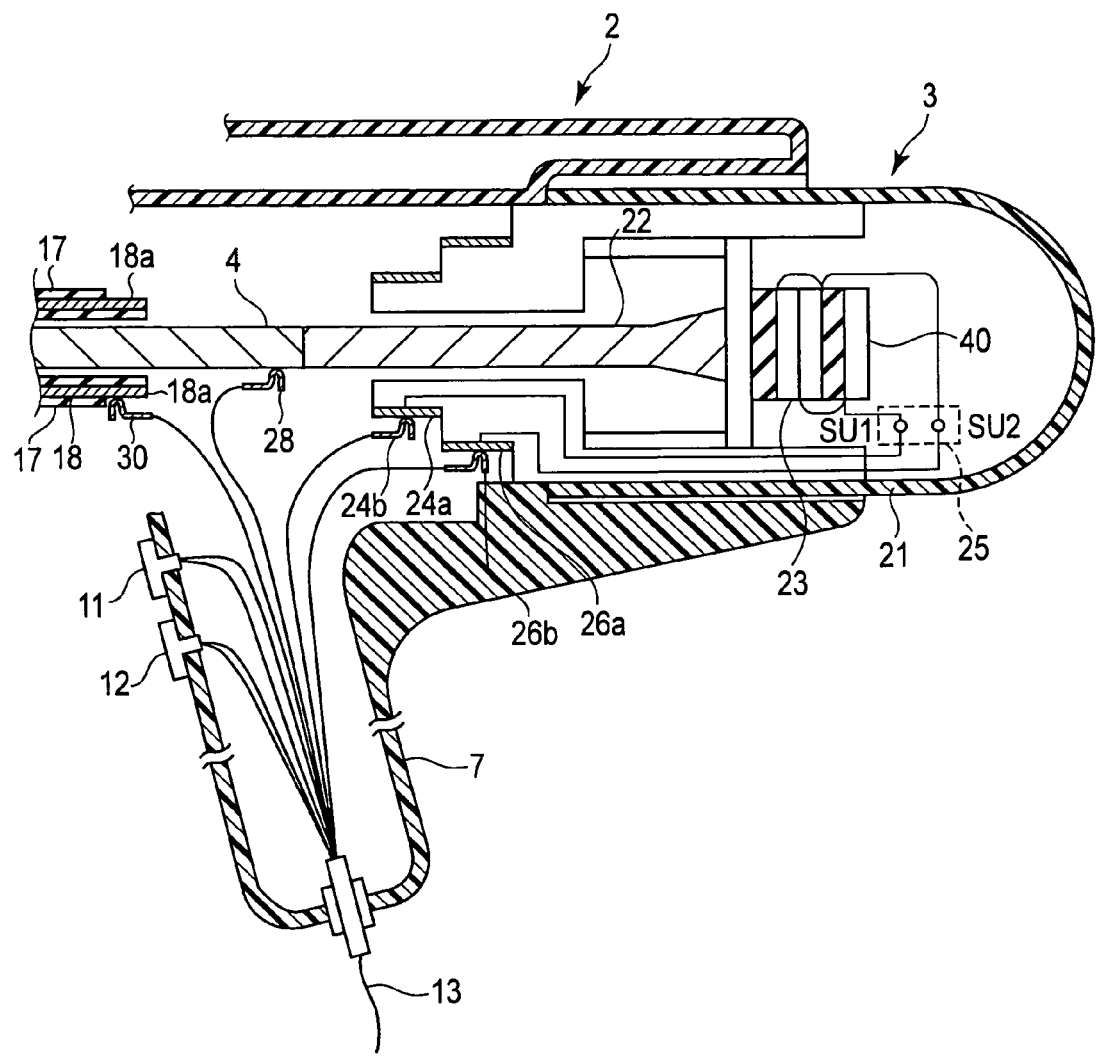
F I G. 8

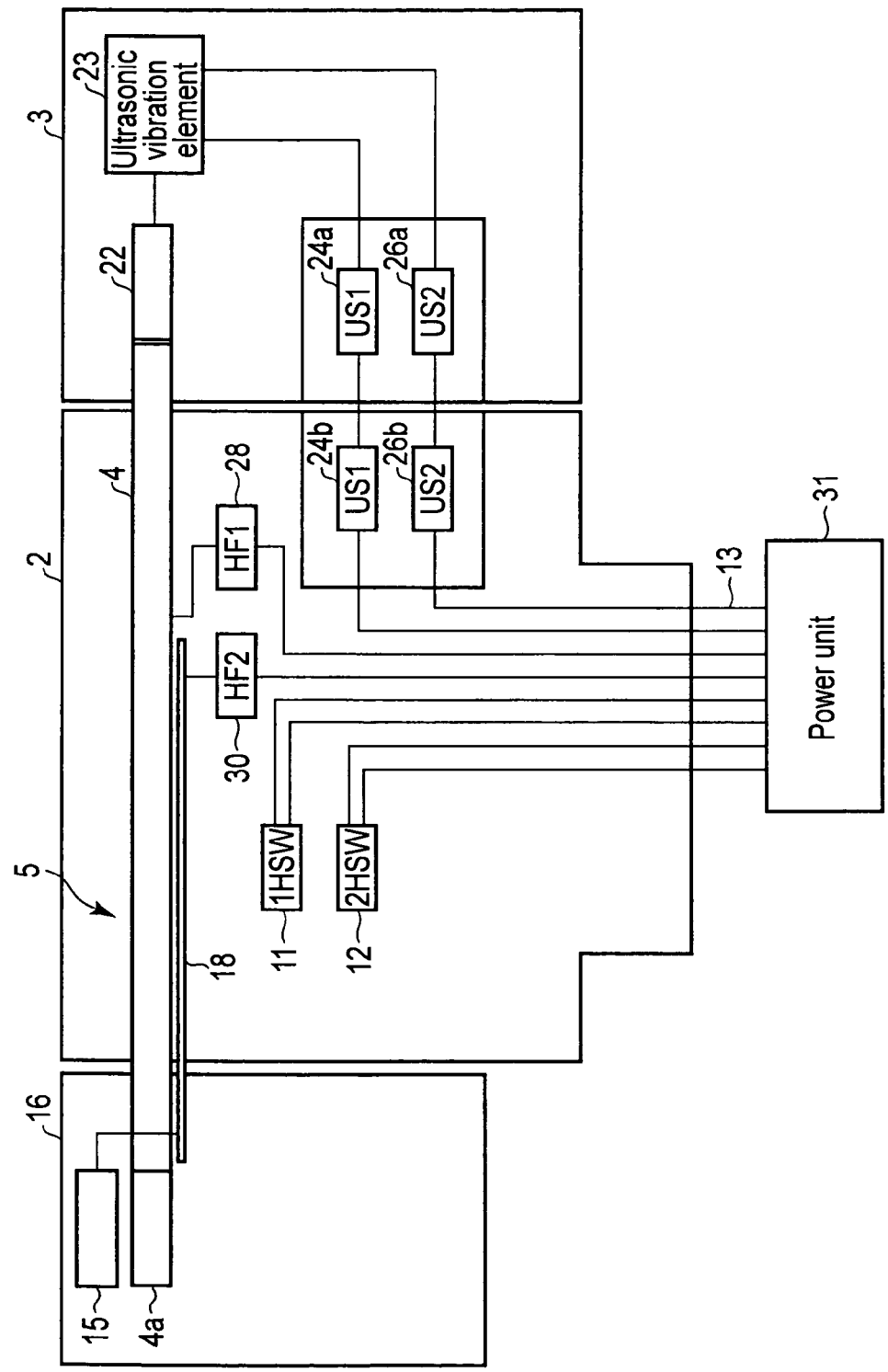
F I G. 9

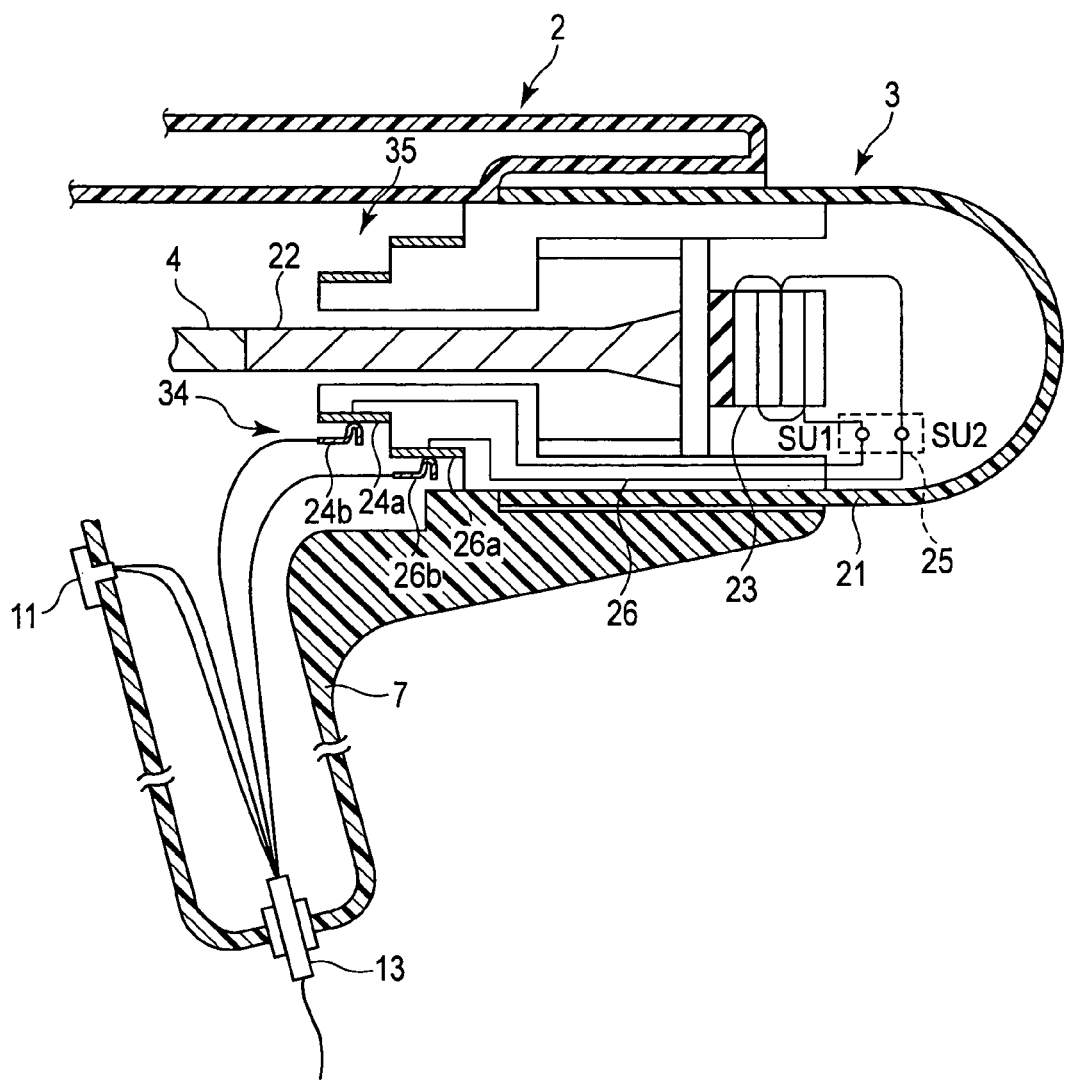
F I G. 10

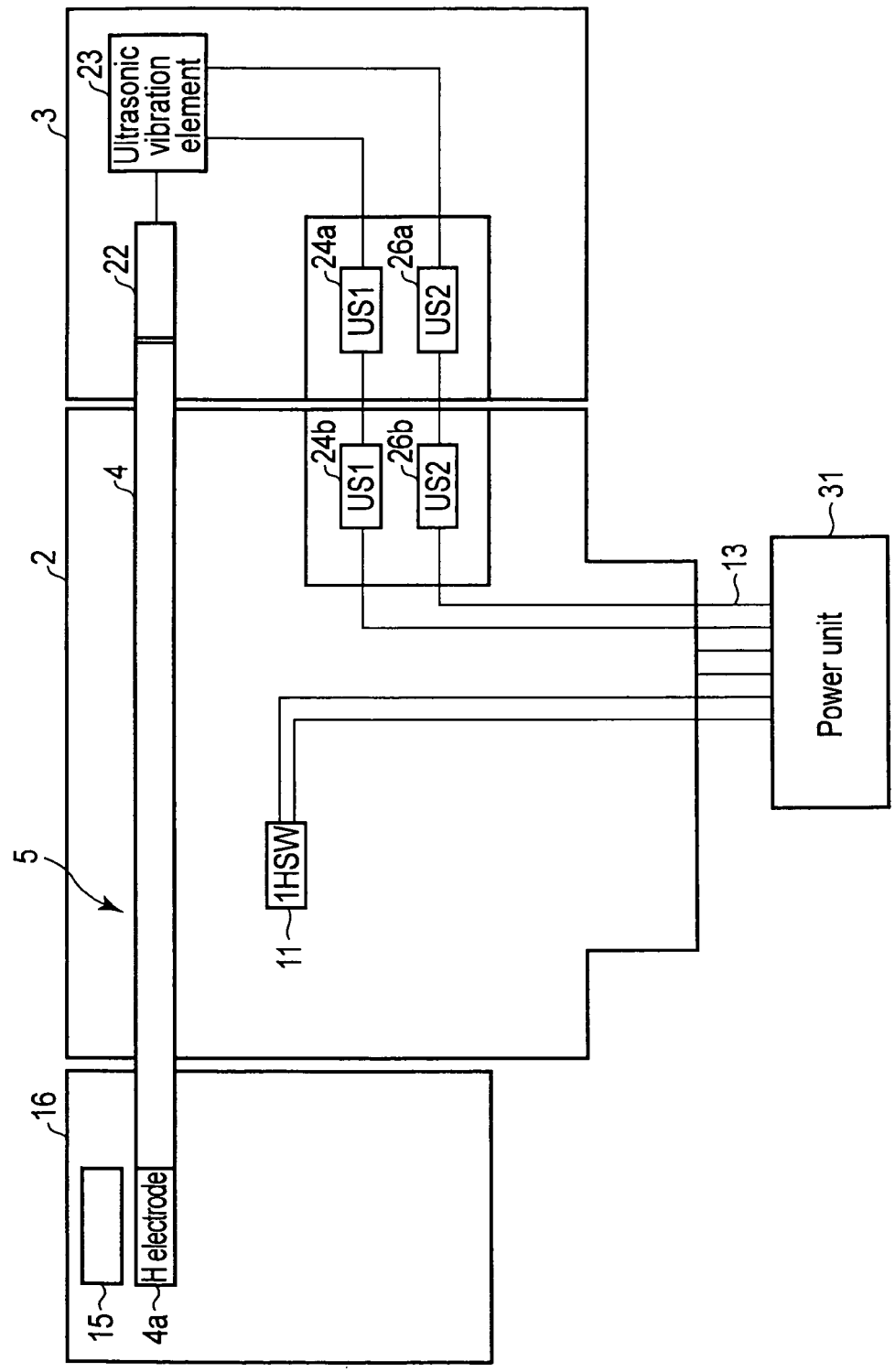
F I G. 11

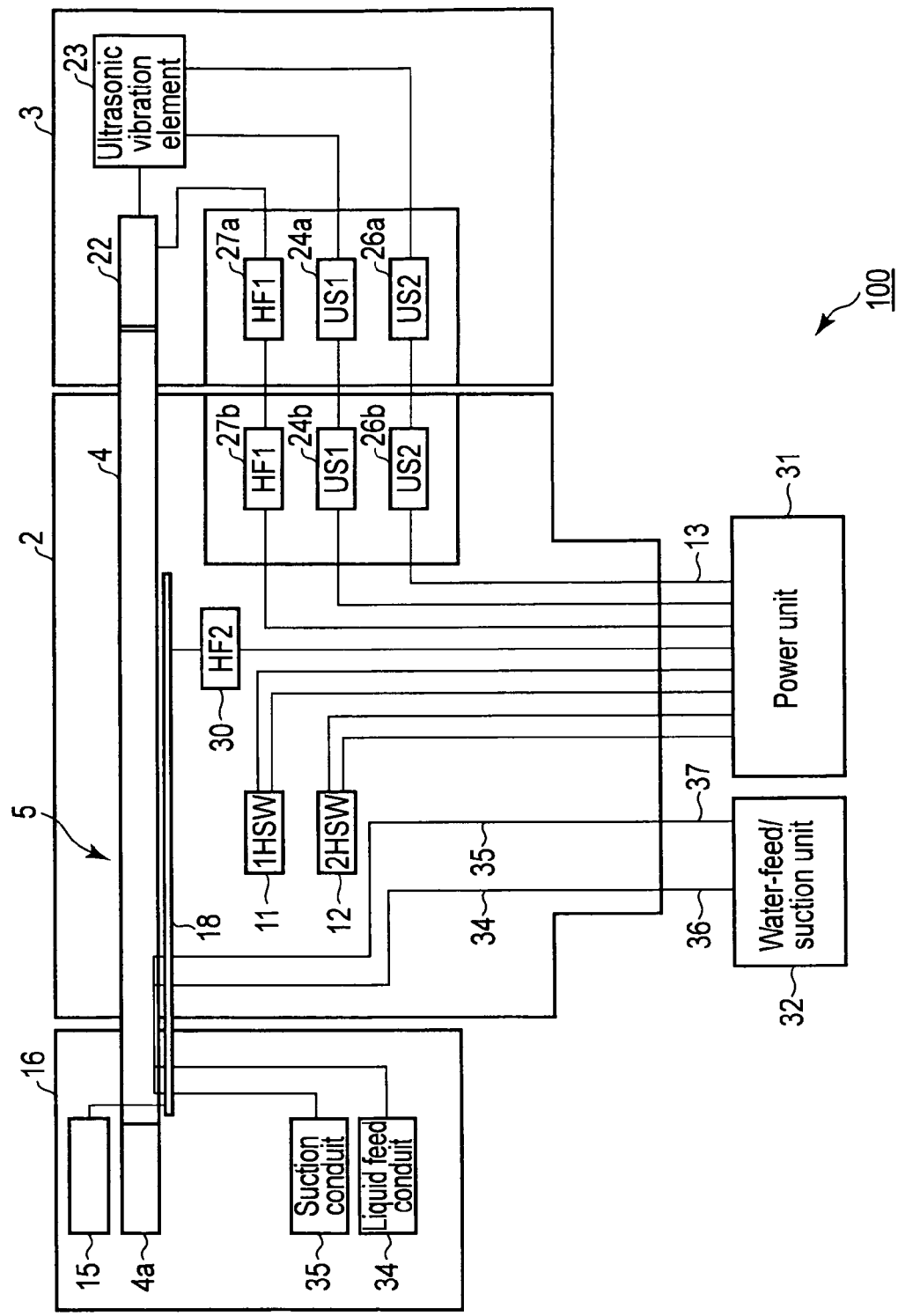
F I G. 13

ULTRASONIC TREATMENT INSTRUMENT USING ULTRASONIC VIBRATIONS

CROSS-REFERENCE TO RELATED APPLICATIONS

This is a Continuation application of PCT Application No. PCT/JP2013/067857, filed Jun. 28, 2013, which was published under PCT Article 21(2) in Japanese.

This application is based upon and claims the benefit of priority from prior U.S. Patent Application No. 61/668,141US, filed Jul. 5, 2012, the entire contents of which are incorporated herein by reference.

BACKGROUND OF THE INVENTION

1. Field of the Invention

The present invention relates to a treatment instrument for performing incision and coagulation treatment on a living body tissue by using ultrasonic vibrations.

2. Description of the Related Art

In general, an ultrasonic coagulation/incision apparatus is known as a treatment instrument for performing incision and coagulation on a target part of a living body tissue, etc., by using ultrasonic vibrations. The treatment on this target part is an act of any one of, for example, incision, resection, perforation, ablation, coagulation, and hemostasis.

As illustrated in FIG. 17, for example, the ultrasonic coagulation/incision apparatus is composed of a handle unit 2 to which a probe 5 is attached, and a transducer unit 3 which generates ultrasonic vibrations.

The transducer unit 3 is detachably attached to the handle unit 2, and is repeatedly usable if sterilization treatment is performed. A forceps-shaped jaw 15 for clamping a target part is provided at a distal end of the probe 5. At a lower part of the handle unit 2, there are provided a stationary handle 7 serving as a hold section for holding by the hand, and a movable handle 8 for opening/closing the jaw 15. An ultrasonic switch 11 for applying ultrasonic vibrations to the target part is disposed in front of the stationary handle 7. Incidentally, the hold section may be configured to be held at two points, which are the stationary handle 7 and movable handle 8.

In addition, the probe 5 is fixed to a rotary knob 6 which is provided in front of the handle unit 2. By rotating the rotary knob 6 in a predetermined angle range, a direction of opening of the jaw 15 is varied, and the target part is clamped and treated from a proper direction. In the transducer unit 3, a vibration element unit is mainly stored, and a cable (power cable) 50 is connected from the outside.

In this structure, at a time of performing treatment, if an operator rotates the rotary knob 6 and varies the direction of opening of the jaw 15, the transducer unit 3 also rotates. As a matter of course, since the cable 50 coupled to the transducer unit 3 also rotates, a twist occurs in the cable 50. Thus, the cable becomes twisted between the transducer unit 3 and a power unit (not shown). Normally, if a twist occurs in the cable, a force acts to reduce the twist, and the amount of a rotational force necessary for a rotating operation of the rotary knob 6 increases, leading to difficulty in operation. Furthermore, if the twist of the cable 50 increases, a winding state occurs in the cable 50, a force acts to reduce the substantial length, and the handle unit 2 is pulled and a shake is caused.

Besides, as illustrated in FIG. 17, in the structure in which the cable 50 is provided in a manner to extend from the transducer unit 3 to the rear (the side opposite to the sheath side), if an unintentional force acts on the cable 50, the treatment instrument is shifted, in some cases, such that the treatment instrument is pulled to the rear side (the transducer unit 3 side), and a slight movement will occur in the jaw 15 due to the shift. Thus, the operator will spend more labor in order to suppress a slight movement of the distal end of the probe 5 and to correctly apply it to the target part.

BRIEF SUMMARY OF THE INVENTION

According to an embodiment of the present invention, there is provided a treatment instrument comprising: a probe unit including a probe configured to transmit ultrasonic vibrations generated by an ultrasonic vibration element; a case section storing the ultrasonic vibration element which is connectable to the probe; a treatment section main body configured to rotatably hold the probe and to couple the ultrasonic vibration element of the case section and the probe of the probe unit when the case section is detachably attached; a contact terminal fixedly provided in the treatment section main body; a power distribution section which is provided in the case section and is a current path to the ultrasonic vibration element; a contact-point member fixedly provided in the case section and electrically connected to the power distribution section; an electrically conductive member configured to maintain a state in which the contact member and the contact-point member are electrically connected, when the contact-point member rotates relative to the contact terminal in accordance with rotation of the probe, at a time of attaching the case section and the treatment section main body; and a cable configured to supply at least driving power to the contact terminal from an outside.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a cross-sectional view illustrating an internal structure example including a transducer unit according to the first embodiment.

FIG. 5 is a cross-sectional view illustrating an internal structure example including a transducer unit according to a second embodiment.

FIG. 6 is a cross-sectional view illustrating a state in which the transducer unit according to the second embodiment is detached from a handle unit.

FIG. 8 is a cross-sectional view illustrating an internal structure example including a transducer unit according to a third embodiment.

FIG. 9 is a view illustrating an example of the entire block structure of the treatment instrument according to the third embodiment.

FIG. 10 is a cross-sectional view illustrating an internal structure example including a transducer unit according to a fourth embodiment.

FIG. 11 is a view illustrating an example of the entire block structure of the treatment instrument according to the fourth embodiment.

FIG. 13 is a view illustrating an example of the entire block structure of the treatment instrument according to the fifth embodiment.

DETAILED DESCRIPTION OF THE PREFERRED EMBODIMENT

Embodiments of the present invention will be described hereinafter in detail with reference to the accompanying drawings.

First Embodiment

Figure 1:
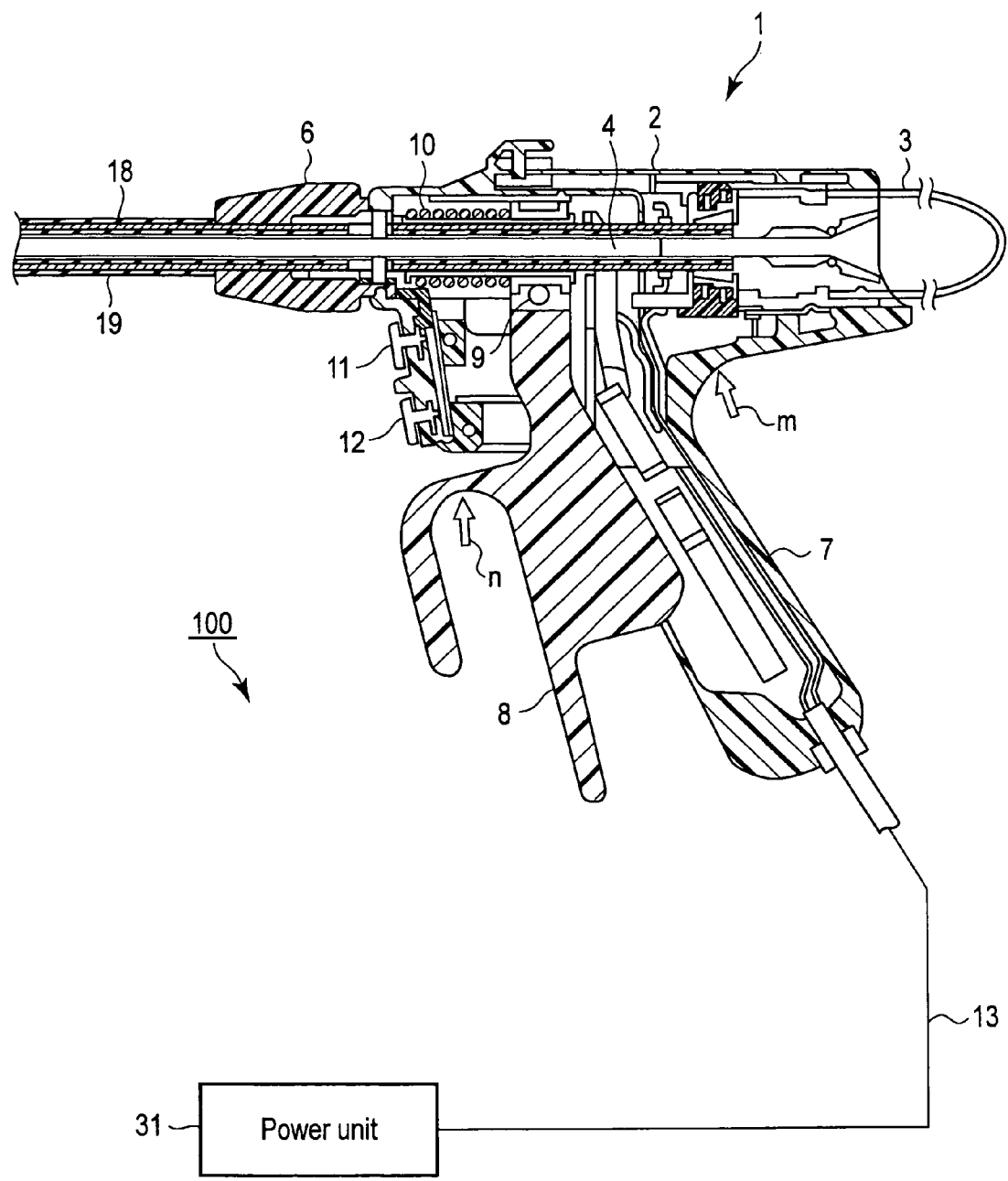
FIG. 1 is a view illustrating an example of the entire system structure of a treatment instrument according to a first embodiment.
Figure 2:
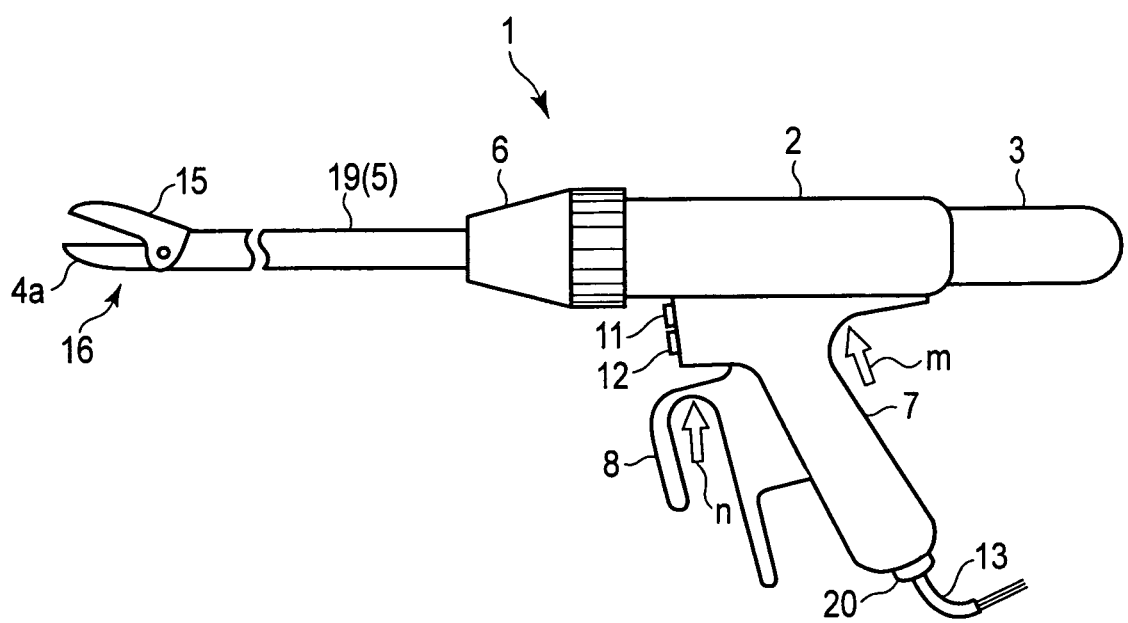
FIG. 2 is a view illustrating a lead-out position of a power cable which supplies power to an ultrasonic vibration element.
Figure 4:
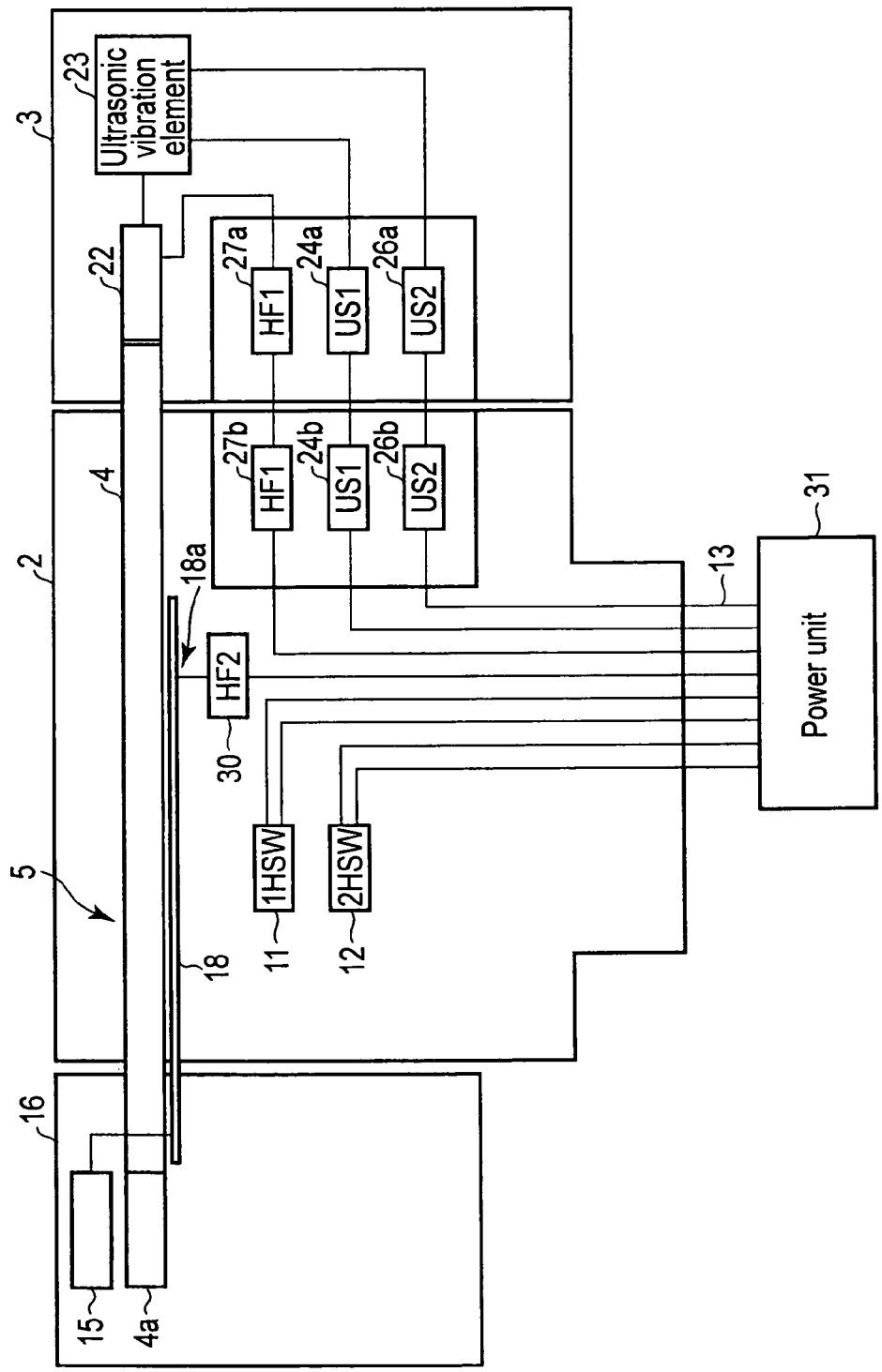
FIG. 4 is a view illustrating an example of the entire block structure of the treatment instrument according to the first embodiment.

FIG. 1 is a view illustrating an example of the entire system structure of a treatment instrument according to a first embodiment. FIG. 2 is a view illustrating a first lead-out position of a power cable which supplies power to an ultrasonic vibration element. FIG. 3 is a view which conceptually illustrates an internal structure example including a cylindrical contact-point member of a transducer unit. FIG. 4 is a view illustrating an example of the entire block structure of the treatment instrument according to the first embodiment. Incidentally, in the description below, a longitudinal direction is a direction connecting a transducer unit 3 and a treatment section 16, in which a probe (sheath unit) extends, and a rotational direction and a width (e.g. a hole) direction are directions which are perpendicular to the longitudinal direction.

A system structure 100 of the present embodiment is composed of a treatment instrument 1 and a power unit 31. The treatment instrument 1 has a pistol shape, and is composed of a handle unit (treatment instrument main body) 2 which is disposable, and a transducer unit 3 which is repeatedly used by being subjected to sterilization treatment. Further, the power unit 31 is connected to the treatment instrument 1 by a power cable 13, and supplies power for driving and a high-frequency signal (a signal having a current and voltage of an arbitrary high frequency) to an ultrasonic vibration element, for instance, a piezoelectric element. A high frequency which is used is a frequency suited to treatment, and is not particularly limited, unless restricted by law. A handle section, which is composed of a stationary handle 7 and a movable handle 8, is provided on a lower side of a main body of the handle unit 2. The stationary handle 7 functions as a grip for holding by the hand. Further, the movable handle 8 is disposed in front of the stationary handle 7, and opens/closes a jaw 15 which is provided on a distal end side of a sheath unit 19. The movable handle 8 is provided to be rotatable about a fulcrum 9 provided near a trunk side of the stationary handle 7 within the unit main body.

A probe unit 5, which is formed of an elongated electrical conductor, is attached to the handle unit 2, and propagates ultrasonic vibrations. This probe unit 5 is covered with the sheath unit 19.

The probe unit 5 is composed of a probe 4 which is formed of an electrical conductor which propagates ultrasonic vibrations and transmits a high-frequency signal, and the treatment section 16. The treatment section 16 is composed of the jaw 15, and a probe distal end portion 4a functioning as a receiver of the jaw 15. The probe distal end portion 4a is a distal end portion of the probe 4, and functions as a bipolar-type high-frequency electrode when a high-frequency signal is applied. The jaw 15 is formed in a shape of a forceps which opens and closes, and a treatment target part can be clamped between the jaw 15 and probe distal end portion 4a.

Besides, a spring 10, which is fitted in the probe 4, has a function of restoring, at a time of extension, the jaw 15 to the open state, and restoring the movable handle 8 to the original position. In addition to this function, the spring 10 functions, at a time of compression, to urge the jaw 15 in the closed state so that the clamped state of the treatment target part may easily be maintained. Specifically, when the urging force by the spring 10 acts on the jaw 15 in the clamped state, the clamped state of the treatment target part by the jaw 15 is maintained even if the hold state of the movable handle 8 is slightly relaxed.

A rear end side of the probe 4 is coupled to a horn section 22 of the transducer unit 3 within the handle unit 2, and is provided such that ultrasonic vibrations and a high-frequency signal (to be described later) are transmitted. In the state in which the jaw 15 is closed, a high-frequency signal is transmitted from the probe distal end portion 4a to the jaw 15. Specifically, when the treatment target part is clamped by the treatment section 16, desired treatment is performed by applying the ultrasonic vibrations or high-frequency signal. In the sheath unit 19, a moving member 18, which has an elongated plate shape or a cylindrical shape along the probe 4 and is formed of an electrical conductor penetrating the inside, is movably disposed. In addition, coating layers, which are formed of insulation members, are formed on outer surfaces and inner peripheral surfaces of the probe 4 and moving member 18. Mutual contact and interference between the inner peripheral surface of the sheath unit 19 and the probe 4 are prevented by an annular elastic member such as a rubber ring (not shown).

The moving member 18 is disposed such that the moving member 18 penetrates the sheath unit 19, has one end coupled to the jaw 15, has the other end engaged with a moving mechanism of the movable handle 8, and moves in the longitudinal direction in accordance with a handle operation. By this movement, the jaw 15 performs an opening/closing operation, that is, a clamping operation, with a location of coupling to the probe distal end portion 4a functioning as a fulcrum. The moving member 18 also has a function of transmitting a high-frequency signal, as will be described later. The moving member 18 does not need to be formed as one body, and may be composed of a plurality of parts. Furthermore, a rotary knob 6 having an annular shape is provided in front of the handle unit 2. This rotary knob 6 is provided to be rotatable relative to the handle unit 2, and the rotary knob 6 rotates the probe 4 within a predetermined angle range by a manual operation of the operator and can freely set the direction of clamping of the jaw. In the rotary knob 6, the probe unit 5, together with the sheath unit 19 penetrating the center, is fixed, as will be described later. For example, with use of a connection metal fitting such as a pin, the probe 4 is engaged with the sheath unit 19 which is fixed to the rotary knob 6.

In the moving member 18, in its structure, an elongated engagement hole is formed in the longitudinal direction, and a pin of a fixing metal fitting, which is fixed to the probe 4, is disposed so as to pass through the engagement hole. The engagement hole extends in the longitudinal direction, and is formed, in its width direction, with a width including a play in addition to the pin diameter. By this structure, the moving member 18 is movable in a manner to reciprocate in the longitudinal direction within the engagement hole in accordance with the handle operation.

However, in the rotational direction of the rotary knob 6, the moving member 18 is restricted by the pin in the width direction of the engagement hole, and follows the rotation of the rotary knob 6. Specifically, the moving member 18 moves forward and backward in the longitudinal direction by the operation of the movable handle 8, and opens/closes the jaw 15, and the moving member 18 rotates in accordance with the rotational operation of the rotary knob 6, and rotates the jaw 15. Although the structure in which the sheath unit 19 and probe unit 5 rotate as one body is illustrated in this example, a structure in which only the probe unit 5 rotates may be adopted.

In addition, a switch (1HSW) 11 and a switch (2HSW) 12 are provided above the movable handle 8. The switch 11 is a switch for applying ultrasonic vibrations and a high-frequency signal to a treatment target part, in order to perform incision and coagulation treatment, and the switch 11 oscillates the ultrasonic vibration element and applies a high-frequency signal (high-frequency current).

Besides, the switch 12 is a switch for applying a high-frequency signal to a treatment target part, in order to perform coagulation treatment, and the switch 12 applies a high-frequency signal (high-frequency current) to the treatment section 16. Switching during the treatment is possible.

In each of the switches 11 and 12, a trigger signal is sent to a power unit or controller side by an ON operation by depression. By this trigger signal, power for driving the ultrasonic vibration element and a high-frequency signal from the power unit 31 are output, respectively, and are applied to the treatment section 16. If an OFF operation for restoring the switch is performed, a trigger signal is sent to the power unit or controller side, and the driving of the ultrasonic vibration element and the output of the high-frequency signal are stopped. Incidentally, in this embodiment, the switches 11, 12 are configured to be provided integral to the stationary handle 7, but are not limited to this configuration. Such a configuration may be adopted that, in place of these switches, a footswitch or the like is separately disposed.

In the description below, in the present embodiment, in the treatment instrument in the state in which the transducer unit 3 is fitted and mounted in the handle unit 2 and the cable is connected, that is, in the treatment instrument in the state in which treatment is performed, the sum of the gravity and a pushing/pulling force (external force) acting on the handle unit 2, which is caused by the cable, is referred to as "load force". In this treatment instrument 1, a center position at which this load force acts is set to be a load force center.

Specifically, this load force center is a center position of the load force in which the external force caused by the connected cable is added to the gravity (weight) acting on the treatment instrument 1, and is a position existing within the treatment instrument. Thus, the center of gravity of the treatment instrument (the center of gravitational force at which the sum of gravitational forces acting on the respective structural parts acts) does not necessarily agree with the load force center.

Incidentally, the cable includes not only the power cable 13, but also a control cable (not shown) for transmitting a control signal, a water supply/discharge tube, etc., that is, includes all cords and tubes connected to the handle unit 2.

In the present embodiment, for example, in the case where the stationary handle 7 has a shape of a butt (pistol grip), a position at which the treatment instrument is balanced between two points, that is, a position (arrow m) on which the base part of the thumb (a part between the thumb and index finger) of the holding hand is hooked, and a position (arrow n) on which the fingertip of another finger (for example, the middle finger in the case where a switch operation is performed by the index finger) is hooked, or the above-described load force center, or a nearby position thereof, is set to be a location of introduction of the cable (the power cable 13 in this example).

In this embodiment, such a design is adopted that the above-described load force center exists near the stationary handle 7, and the power cable 13 is introduced into the inside from the bottom part of the stationary handle 7. In the structure illustrated in FIG. 1, the power cable 13 is configured to be directly led into the handle unit 2. Alternatively, as illustrated in FIG. 2, such a structure may be adopted that the power cable 13 is detachably attached via a connector 20.

Next, the transducer unit 3 is described.

As illustrated in FIG. 1 and FIG. 3, the transducer unit 3 includes, within a case 21, a horn section 22 which constitutes a vibration element unit, an ultrasonic vibration element 23, and a power distribution section 25.

An outer peripheral surface of the horn section 22 and an inner wall surface of a through-hole are set such that a predetermined gap is provided so as not to affect generated ultrasonic waves. In the meantime, in the case of supporting the horn section 22, the horn section 22, in principle, is supported at a sound node (syllable) portion. Incidentally, the power distribution section 25 is not indispensable, and may not be provided. In addition, a plurality of annular stepped portions, which are tapered toward the horn section 22, are provided at a coupling portion with the handle unit 2 at an internal distal end of the transducer unit 3. Cylindrical contact-point members 24a, 27a, 26a, which are formed of electrically conductive members and function as substantially cylindrical power delivery members, are formed on the surfaces of these stepped portions. The cylindrical contact-point member shown in FIG. 3 does not necessarily need to have a perfect annular shape. If the range of rotation is covered, the cylindrical contact-point member may have a rounded curved plate shape including a slit portion, which is not a complete annular shape, or may be a curved plate shape of a semicircle or less.

In addition, contact terminals 24*b*, 27*b*, 26*b*, which are formed of brushes or the like, are fixedly provided in the handle unit 2, and are in contact with, and electrically connected to, the cylindrical contact-point members 24*a*, 27*a*, 26*a*. Specifically, an electrical contact-point structure, which rotatably slides, is constituted by the cylindrical contact-point members 24*a*, 27*a*, 26*a* and the contact terminals 24*b*, 27*b*, 26*b*. Besides, the contact terminals 24*b*, 27*b*, 26*b* are connected to the power cable 13 via internal wiring.

Furthermore, the moving member 18 in the sheath 19 constitutes a part of a transmission path (a path for feedback current) of a high-frequency signal (to be described later). The distal end side of the moving member 18 is connected to the jaw 15, as described above, and the proximal end side of the moving member 18 is provided with a cylindrical contact-point member 18*a*, which is in contact with a contact terminal 30, thus constituting an electrical connection from the jaw 15 to the contact terminal 30.

In this structure, the moving member 18, which moves in the longitudinal direction by the operation of the movable handle 8, is used as a current path. In the electrical connection between the cylindrical contact-point member 18*a* and contact terminal 30, since these rotates as one body, if the electrical connection is proper when the transducer unit 3 is connected to the handle unit 2, the connection state is maintained also when the jaw 15 is rotated.

To begin with, the structure relating to ultrasonic treatment is described.

The cylindrical contact-point members 24*a*, 26*a* are a part of the current path through which AC driving power for driving the ultrasonic vibration element 23 flows via internal wiring. The cylindrical contact-point members 24*a*, 26*a* are electrically connected to the power distribution section 25 (US1, US2). The power distribution section 25 makes connection to electrodes of the ultrasonic vibration element 23 by wiring.

The ultrasonic vibration element 23 outputs, for example, a predetermined frequency (number of vibrations) by using stacked piezoelectric elements. The structural dimensions, etc. of the horn section 22 are designed so as to obtain an amplification (e.g. transformation ratio) to a desired vibration speed. Ultrasonic waves, which are generated by the horn section 22, are transmitted to the treatment section 16 via the probe 4. The cylindrical contact-point members 24*a*, 26*a* are put in contact with the contact terminals 24*b*, 26*b*, receive driving power which is supplied from the power unit 31 via the power cable 13 and power distribution section 25, and supplies the power to the ultrasonic vibration element 23.

As illustrated in FIG. 4, the current path of the ultrasonic driving power is as follows: power unit 31-power cable 13-contact terminal (US1) 24*b*-cylindrical contact-point member (US1) 24*a*-(power distribution section 25)-ultrasonic vibration element 23-(power distribution section 25)-cylindrical contact-point member (US2) 26*a*-contact terminal 26*b* (US2)-power cable 13-power unit 31. Incidentally, since the driving power of the ultrasonic vibration element (piezoelectric element) is alternating current (AC), the flow of current is reversed by the positive/negative amplitude.

Next, the structure relating to high-frequency treatment is described.

The cylindrical contact-point member 27*a* of the transducer unit 3 is electrically connected to the power distribution section 25 (HF) via internal wiring. The power distribution section 25 makes connection to the horn section 22 by wiring, or makes connection to an electrical conduction part 40 which is electrically connected to the horn section 22. A high-frequency signal (high-frequency current), which has been supplied to the electrical conduction part 40, is output to the probe distal end portion 4*a* of the bipolar electrode from the horn section 22 via the probe 4. Then, the high-frequency signal flows from the probe distal end portion 4*a* to the jaw 15 via a treatment target part which is clamped. The high-frequency signal, which has been received by the jaw 15, flows to the moving member 18 within the sheath 19, and is transmitted from the cylindrical contact-point member 18*a* of the moving member 18 to the contact terminal 30. The high-frequency signal flows from the contact terminal 29 to the power cable 13 via internal wiring and is fed back to the power unit 31. Incidentally, the electrical conduction part 40 is not indispensable.

As illustrated in FIG. 4, the transmission path of the high-frequency signal is as follows: power unit 31-power cable 13-contact terminal (HF1) 27*b*-cylindrical contact-point member (HF1) 27*a*-(electrical conduction part 40)-horn section 22-probe 4-probe distal end portion (bipolar electrode) 4*a*-treatment target part-jaw 15-moving member 18-cylindrical contact-point member 18*a*-contact terminal (HF2) 30-power cable 13-power unit 31.

When the transducer unit 3 of the present embodiment has been mounted in the handle unit 2, the transducer unit 3 puts the probe 4 and horn section 22 in contact, is coupled to the sheath unit 19 and probe unit 5, and rotates with them when the rotary knob 6 is rotated. The mounting in the handle unit 2 may be performed by fixation by screw engagement, by forming screw portions on mutual contact parts of the handle unit 2 and transducer unit 3. Alternatively, such a configuration may be adopted that detachable fixation is made by using an engaging part by a fixating metal fitting such as a hook.

In this rotary switch structure, when the rotary knob 6 has been rotated, the cylindrical contact-point members 24*a*, 26*a*, 27*a* and 18*a* slidingly move in a go-around manner in a state of contact with the fixed contact terminals 24*b*, 26*b*, 27*b* and 30.

As has been described above, according to the present embodiment, since the location of introduction of the power cable into the treatment instrument is disposed at the load force center or thereabout, the entire apparatus is balanced and the operability is enhanced. In particular, in this embodiment, since the position of hold by the operator is disposed at the load force center of the treatment instrument and the position of introduction of the power cable is disposed at the load force center or thereabout, well-balanced hold is realized and, moreover, the operability of the jaw is improved.

In particular, in the prior art, when a shift or shake has occurred in the power cable which is wired from the power supply, an intermediate location held by the hand (finger) function as a fulcrum in the linear positional relationship between the position of introduction of the power cable in the treatment instrument and the treatment section, and if the power cable is pulled downward, such an action occurs that the treatment section rises upward, and it is necessary to suppress this rising by the finger or wrist. According to the treatment instrument of this embodiment, when the power cable is similarly pulled downward, since the entirety of the treatment instrument is pulled down, the suppression can be made by the force of the arm, which is easier than the suppression by the finger or wrist and causes less fatigue. In particular, since the entirety of the treatment instrument is to be pulled down, the distance of movement of the distal end portion is shorter than the distance of movement of the distal end portion by the rising, and a load on a fine therapy technique is reduced for the operator.

In addition, in the conventional pistol-type treatment instrument which is held at the butt (pistol grip), since the power cable extends over the holding arm, a situation in which the operation is hindered occurs depending on the condition of wiring of the power cable. However, according to the present embodiment, since the position of introduction of the power cable is provided at the bottom part of the stationary handle, the power cable does not hinder the operation, and the operability is improved.

Furthermore, in the present embodiment, the rotary electrode structure by the cylindrical contact-point members, which are substantially cylindrical, and the contact terminals is mounted in the handle unit. Thereby, when the rotary knob is rotated in order to adjust the direction of opening of the jaw, a twist of the cable, which poses the problem in the prior art in the case of directly introducing the power cable, does not occur, the load on the treatment instrument due to the power cable is reduced, and the operability is further improved.

Besides, since the switch of ultrasonic treatment and the switch of high-frequency treatment are juxtaposed on the handle unit 2, the change-over operation is easy, and, since the load force center is present near the handle, a shake of the probe at the time of the change-over operation by a single-handed operation can be suppressed to a minimum.

Moreover, the electrical connection structure by the cylindrical contact-point members, which are provided on the transducer unit 3 and are adaptive to rotation, and contact terminals is used. Thus, even when the jaw 15 has rotated at any angle within the movable range of the sheath unit 19, it is possible to realize, at a time of treatment, an electrically connected state of the current path of ultrasonic driving power and the transmission path of a high-frequency signal. Therefore, regardless of the rotation of the rotary knob 6, ultrasonic vibrations can be generated and a high-frequency signal can be applied. Even when the direction of opening of the jaw 15 has been varied, the contact terminals 24b, 26b, 27b and 30 slidingly move over, while being in a state of contact with, the cylindrical contact-point members 24a, 26a, 27a and 18a. Thus, the supply of power and the application of the high-frequency signal are not shut off, and the treatment can be performed without suspending the treatment operation or performing re-clamping of the treatment target part by the jaw 15.

Second Embodiment

Next, a second embodiment is described.

Figure 7:
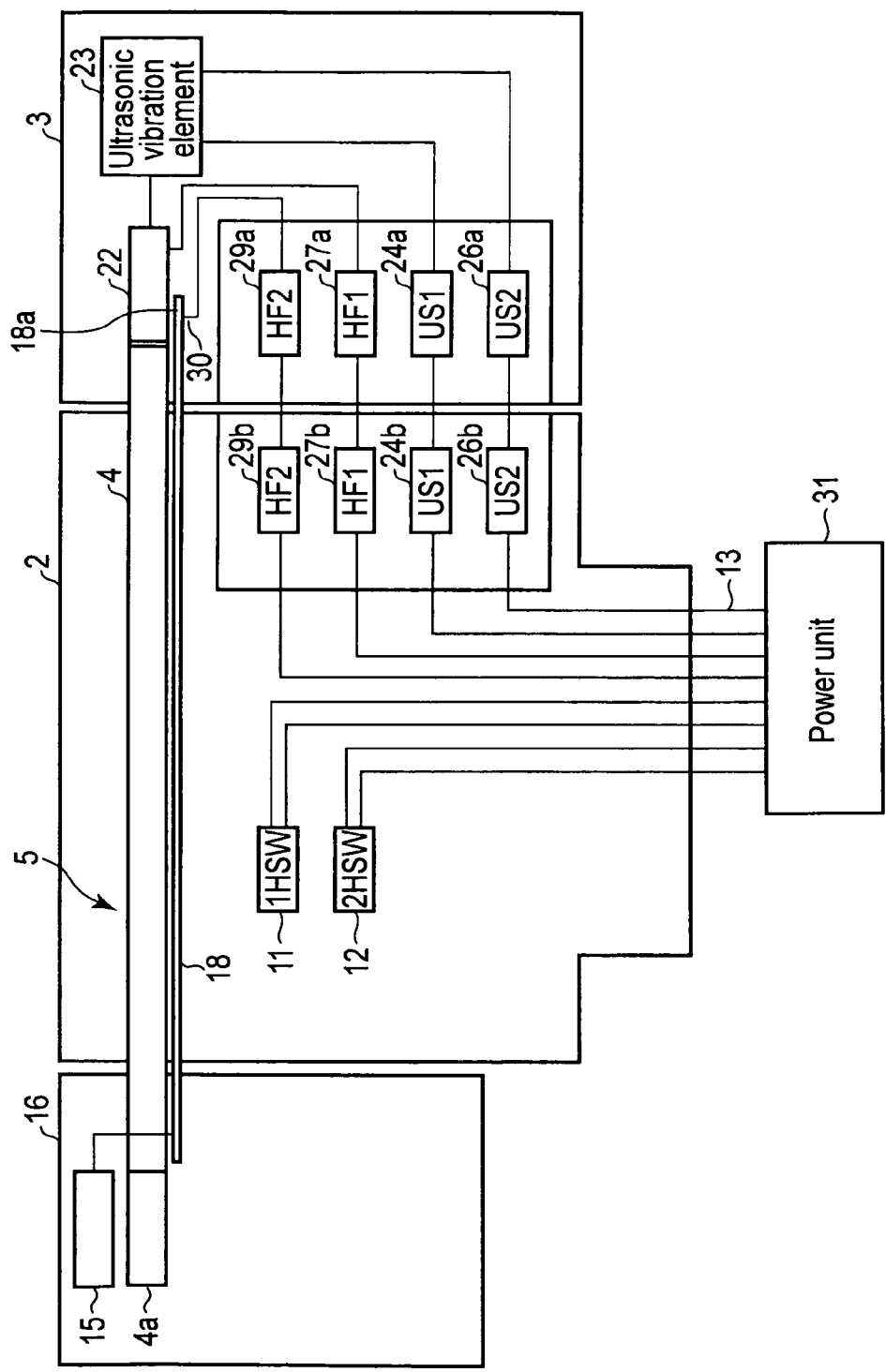
FIG. 7 is a view illustrating an example of the entire block structure of the treatment instrument according to the second embodiment.

The present embodiment, compared to the above-described first embodiment, has a structure in which the transmission path of the high-frequency signal returns from the treatment section 16 via the moving member 18 and a contact terminal provided on the transducer unit 3. FIG. 5 is a cross-sectional view illustrating an internal structure example including a transducer unit according to a second embodiment. FIG. 6 is a cross-sectional view illustrating a state in which the transducer unit according to the second embodiment is detached from a handle unit. FIG. 7 is a view illustrating an example of the entire block structure of the treatment instrument according to the second embodiment. As regards the structural parts of this embodiment, the same structural parts as in the above-described first embodiment are denoted by like reference numerals, and a description thereof is omitted here.

In the description below, the current path of power supply, which is used for ultrasonic treatment, is the same as in the above-described first embodiment, and a description thereof is omitted here.

As illustrated in FIG. 5, as regards the cylindrical contact-point members on the transducer unit 3, cylindrical contact-point members 24a, 26a, 27a and 29a are disposed stepwise in a manner to narrow from the outer peripheral side to the inner side. On the handle unit 2 side, contact terminals 24b, 26b, 27b and 29b are disposed so as to come in contact with these cylindrical contact-point members when the transducer unit 3 is attached.

In the transmission path of the high-frequency signal, the cylindrical contact-point member 27a, like the above-described cylindrical contact-point member 29a, is connected via internal wiring to the horn section 22, or connected to the electrical conduction part 40 which is electrically connected to the horn section 22.

Further, the cylindrical contact-point member 29a penetrates an insulative internal part of the transducer unit 3, and a contact terminal 30 is provided in a manner to project to the inner wall surface of the hole in which the horn section 22 is disposed.

This contact terminal 30 is put in contact with, and is electrically connected to, the cylindrical contact-point member 18a of the moving member 18. As regards the cylindrical contact-point member 29a and contact terminal 30, like the above-described first embodiment, when the jaw 15 is in the open state, the cylindrical contact-point member 18a advances in the longitudinal direction by the movement of the cylindrical contact-point member 18a, and the cylindrical contact-point member 18a and contact terminal 30 are separated.

In addition, in the closed state of the jaw 15, the cylindrical contact-point member 18a retreats in the longitudinal direction, and the cylindrical contact-point member 18a and contact terminal 30 come in contact and are electrically connected, thus constituting a transmission path for feeding back the high-frequency signal.

As illustrated in FIG. 6, when the transducer unit 3 is detached from the handle unit 2, the contact terminals 24b, 26b, 27b, 29b and 30 and the cylindrical contact-point members 24a, 26a, 27a, 29a and 18a are, separated and are also electrically isolated.

As illustrated in FIG. 7, the transmission path of the high-frequency signal is as follows: power unit 31-power cable 13-contact terminal (HF1) 27b-cylindrical contact-point member 27a-(electrical conduction part 40)-horn section 22-probe 4-probe distal end portion (bipolar electrode) 4a-treatment target part-jaw 15-moving member 18-cylindrical contact-point member 18a-contact terminal 30-cylindrical contact-point member 29a-contact terminal (contact terminal) 29b-power cable 13-power unit 31.

According to the present embodiment, the same advantageous effects as in the above-described first embodiment can be obtained. Furthermore, since the contact terminal for the transmission path of the feedback side of the high-frequency signal is provided on the side of the transducer unit 3 which is re-used, the structure of the handle unit 2 is simplified, and the manufacturing process cost and the cost of parts can be reduced.

Third Embodiment

Next, a third embodiment is described.

The present embodiment has a structure of the transmission path in which the high-frequency signal is applied from the probe 4 (or probe 5), instead of the horn section 22 in the above-described first embodiment. FIG. 8 is a cross-sectional view illustrating an internal structure example including a transducer unit according to the third embodiment. FIG. 9 is a view illustrating an example of the entire block structure of the treatment instrument according to the third embodiment. As regards the structural parts of this embodiment, the same structural parts as in the above-described first embodiment are denoted by like reference numerals, and a description thereof is omitted.

As illustrated in FIG. 8, as regards the cylindrical contact-point members on the transducer unit 3 of this embodiment, cylindrical contact-point members 24a, 26a are disposed stepwise in a manner to narrow from the outer peripheral side to the inner side. Contact terminals 24b, 26b on the handle unit 2 side are disposed in association with these cylindrical contact-point members 24a, 26a. In the description below, the current path of power supply, which is used for ultrasonic treatment, is the same as in the above-described first embodiment, and a description thereof is omitted here.

In the transmission path of the high-frequency signal, fixed contact terminals 28, 30 are provided on the handle unit 2 side. The contact terminal 28 is put in contact with, and is electrically connected to, the probe 4 which is formed of a cylindrical, electrically conductive member, and applies a high-frequency signal, which has been supplied from the power cable 13, to the probe 4. In the meantime, in this example of the structure, the contact terminal 28 is in direct contact with the probe 4. However, in the case where the probe unit 5 is assembled of a plurality of structural parts, it is possible that the contact terminal 28 is connected to some part which is formed of an electrically conductive member that is in slidable contact with the probe 4. In addition, the cylindrical contact-point member 18a and contact terminal 30 are the same as in the above-described first embodiment, and a description thereof is omitted. As illustrated in FIG. 9, the transmission path of the high-frequency signal is as follows: power unit 31-power cable 13-contact terminal (HF1) 28-probe 4-bipolar electrode 4a-treatment target part-jaw 15-conductive member 18-cylindrical contact-point member 18a-contact terminal 30-power cable 13-power unit 31.

According to the present embodiment, the same advantageous effects as in the above-described first embodiment can be obtained. In addition, since the transmission path of the high-frequency signal does not pass through the transducer unit 3, the reduction in size can be realized, and this embodiment is also used for a handle unit of a type in which there is no transmission path of a high-frequency signal, which will be described later.

Fourth Embodiment

Next, a fourth embodiment is described.

The present embodiment is a treatment instrument which performs only ultrasonic treatment. FIG. 10 is a cross-sectional view illustrating an internal structure example including a transducer unit according to the fourth embodiment. FIG. 11 is a view illustrating an example of the entire block structure of the treatment instrument according to the fourth embodiment.

As regards the structural parts of this embodiment, the same structural parts as in the above-described first embodiment are denoted by like reference numerals, and a description thereof is omitted.

The handle unit 2 is composed of the probe 4, probe treatment portion 4a, jaw 15, and sheath unit 19 covering the probe 4. The probe treatment portion 4a and the jaw 15 clamp a treatment target part and perform ultrasonic treatment on the treatment target part. The rear end side of the probe 4 is put in contact with the horn section 22 of the transducer unit 3 within the handle unit 2, and ultrasonic vibrations are transmitted.

Furthermore, by the above-described structure, the above-described rotary knob (not shown) for rotating the sheath unit 19 and probe 4 as one body is provided in front of the handle unit 2. This rotary knob rotates the probe 4 within a predetermined angle range by a manual operation of the operator and can freely set the direction of clamping of the jaw 15.

In addition, the movable handle (not shown), which opens/closes the jaw 15, and the ultrasonic application switch (1HSW) 11 are provided on the stationary handle 7 which is provided on the lower side of the main body of the handle unit 2.

Next, the transducer unit 3 is described.

As illustrated in FIG. 10, the transducer unit 3 includes, within the case 21, the horn section 22 which constitutes the vibration element unit, the ultrasonic vibration element 23, and the power distribution section 25. Cylindrical contact-point members 24a, 26a on the transducer unit 3 are disposed stepwise in a manner to narrow from the outer peripheral side to the inner side. On the handle unit 2 side, contact terminals 24b, 26b, which are put in slidable contact with these cylindrical contact-point members 24a, 26a are disposed.

The cylindrical contact-point members 24a, 26a are electrically connected to the power distribution section 25 (US1, US2) via internal wiring. The power distribution section 25 makes connection to electrodes of the ultrasonic vibration element 23 by wiring, and supplies power for driving.

The power distribution section 25 is not indispensable and may be omitted, and direction connection may be made at a location of a sound node of ultrasonic in the horn section 22.

In the structure by the cylindrical contact-point members 24a, 26a and contact terminals 24b, 26b when the rotary knob 6 is rotated, the probe 4 and horn section 22 rotate, in a close contact state, together with the sheath unit 19 as one body, as described above. Thus, the contact terminals 24b, 26b slidingly move in a state of contact with the fixed cylindrical contact-point members 24a, 24b.

Accordingly, since the state of electrical connection is maintained even when the direction of opening/closing of the jaw 15 is rotated in accordance with treatment, the treatment can be performed by clamping the treatment target part from a desired direction.

As illustrated in FIG. 11, the current path of the ultrasonic driving power is as follows: power unit 31-power cable 13-contact terminal (US1) 24b-cylindrical contact-point member (US1) 24a-(power distribution section 25)-piezoelectric element 23-(power distribution section 25)-cylindrical contact-point member 26a (US2)-contact terminal 26b (US2)-power cable 13-power unit 31. Incidentally, since the driving power of the piezoelectric element is AC, the flow of current is reversed by the positive/negative amplitude.

In the structure of this embodiment, the position of introduction of the power cable 13 is disposed (first position of introduction) at the load force center, or thereabout, of the treatment instrument in the state in which the transducer unit 3 is fitted and mounted in the handle unit 2, that is, the treatment instrument in the state in which treatment is performed. For example, in the case where the hold part has a shape of a butt (pistol grip), the location of introduction of the power cable 13 is disposed at a position at which the treatment instrument is balanced between two points, which are the base part of the thumb (a part between the thumb and index finger) of the holding hand and the fingertip of another finger (for example, the index finger), or the load force center between the two points, or thereabout. Incidentally, in the use state in which the power cable is connected to the treatment instrument, it is desirable that the weight of the entire treatment instrument acts on the entirety of the arm via that part of the stationary handle 7, which is in contact with the base part of the thumb and index finger. The structure is not necessarily restricted to the case in which the location itself of introduction of the power cable 13 agrees with the load force center of the treatment instrument 1.

In this embodiment, such a design is adopted that the load force center of the entire apparatus exists near the stationary handle 7, and the power cable 13 is introduced into the inside from the bottom part of the stationary handle 7. In the structure illustrated in FIG. 1, the power cable 13 is configured to be directly led into the handle unit 2. Alternatively, as illustrated in FIG. 2, such a structure may be adopted that the power cable 13 is detachably attached via the connector 20. In the structure of FIG. 10, the power cable 13 is directly led into the handle unit 2, but, as illustrated in FIG. 2, such a structure may be adopted that the power cable 13 is detachably attached via the connector 20.

As has been described above, according to the present embodiment, since the location of introduction of the power cable into the treatment instrument is disposed at the load force center of the treatment instrument, or thereabout, the entire apparatus is balanced and the operability is enhanced. In particular, in this embodiment, since the position of hold by the operator is disposed at the load force center of the treatment instrument and the position of introduction of the power cable is disposed at the load force center or thereabout, well-balanced hold is realized and, moreover, the operability of the jaw is improved.

Furthermore, in the present embodiment, the rotary electrode structure by the cylindrical contact-point members, which are substantially cylindrical, and the contact terminals is mounted in the handle unit. Thereby, when the rotary knob is rotated in order to adjust the direction of opening of the jaw, a twist of the cable, which poses the problem in the prior art in the case of directly introducing the power cable, does not occur, the load on the treatment instrument due to the power cable is reduced, and the operability is further improved.

Fifth Embodiment

Next, a fifth embodiment is described.

Figure 12:
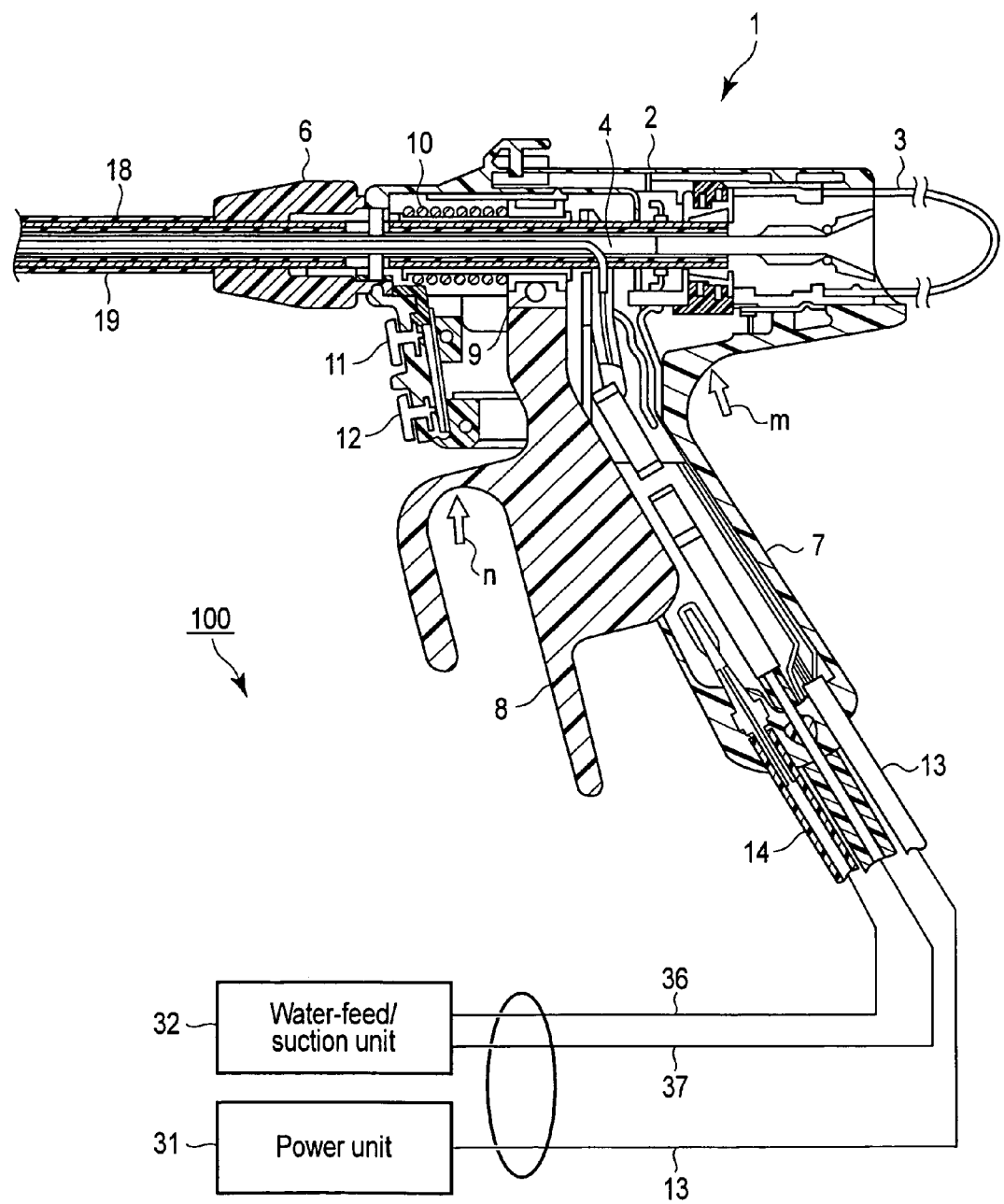
FIG. 12 is a view illustrating an example of the entire system structure of a treatment instrument according to a fifth embodiment.

FIG. 12 is a view illustrating an example of the entire system structure of a treatment instrument according to the fifth embodiment. FIG. 13 is a view illustrating an example of the entire block structure of the treatment instrument according to the fifth embodiment. Incidentally, in this structure, the same structural parts as in the above-described first embodiment are denoted by like reference numerals, and a description thereof is omitted. In addition, the structure and treatment, which use either ultrasonic vibrations or high-frequency vibrations, are exactly the same as in the above-described embodiment, and a description thereof is omitted here.

In addition to the structure of the first embodiment, the present embodiment has a structure in which the position of introduction of a liquid-feed conduit 36 and a suction conduit 37 for water feed and suction is disposed at the position of introduction of the power cable 13. A water-feed/suction unit 32 feeds water or a liquid for cleaning, etc., which is used during an operation, and performs suction for exhausting a liquid in the vicinity of a treatment target part. In this example, the part of introduction of the liquid-feed conduit and suction conduit is disposed in the case where the bottom part of the stationary handle 7 is the load force center of the treatment instrument. A liquid-feed conduit 34 and a suction conduit 25 in the handle unit 2 are formed of flexible tubes, for instance, resin tubes, and are introduced into the inside from the bottom part of the stationary handle 7, as illustrated in FIG. 12, and are, in particular, arranged so as to avoid the movable range of the movable handle 8 and to penetrate the probe 4 to the probe distal end portion (bipolar electrode) 4a at the distal end portion. In order to prevent a load from acting on the tubes by the rotation of the tube 4 when the tubes are introduced into the probe 4, a slackness (play) is given, or the shape (e.g. a notch) of the probe 4 may be adaptively varied.

According to the embodiment, the position of introduction of the conduits for water feed and suction is disposed at the load force center of the treatment instrument or thereabout, like the power cable 13. Thereby, the entire apparatus is balanced and the operability is enhanced. In particular, in this embodiment, since the position of hold by the operator is disposed at the load force center of the treatment instrument and the position of introduction of the power cable 13 is disposed at the load force center or thereabout, well-balanced hold is realized and, moreover, the problem of a shift is solved, and the operability of the jaw 15 is improved.

In this structure, the parts of introduction of the power cable, liquid-feed conduit 34 and suction conduit 35 are disposed together at the bottom part of the stationary handle 7. Thus, the water-feed/suction unit 32 can be disposed near the power unit 31, and the above-described power cable, liquid-feed tube 36 and suction tube 37 can be handled as a single integrated cable. The single integrated cable has such an advantage that when this cable is wired over the floor, the behavior of the operator's arm and the standing position of the operator are made better, and it is possible to prevent forgetting to connect the cables and tubes. Incidentally, in the treatment instrument of this embodiment, the water-feed and suction are not necessarily provided as a pair, and either of them may be replaced with a function of another treatment instrument.

Furthermore, in the structure of FIG. 12, the power cable 13, liquid-feed tube 36 and suction tube 37 are directly led into the stationary handle. However such a structure may be adopted that each of them or all of them, as a whole, are detachably attached via a connector.

Sixth Embodiment

Next, a sixth embodiment is described.

Figure 14:
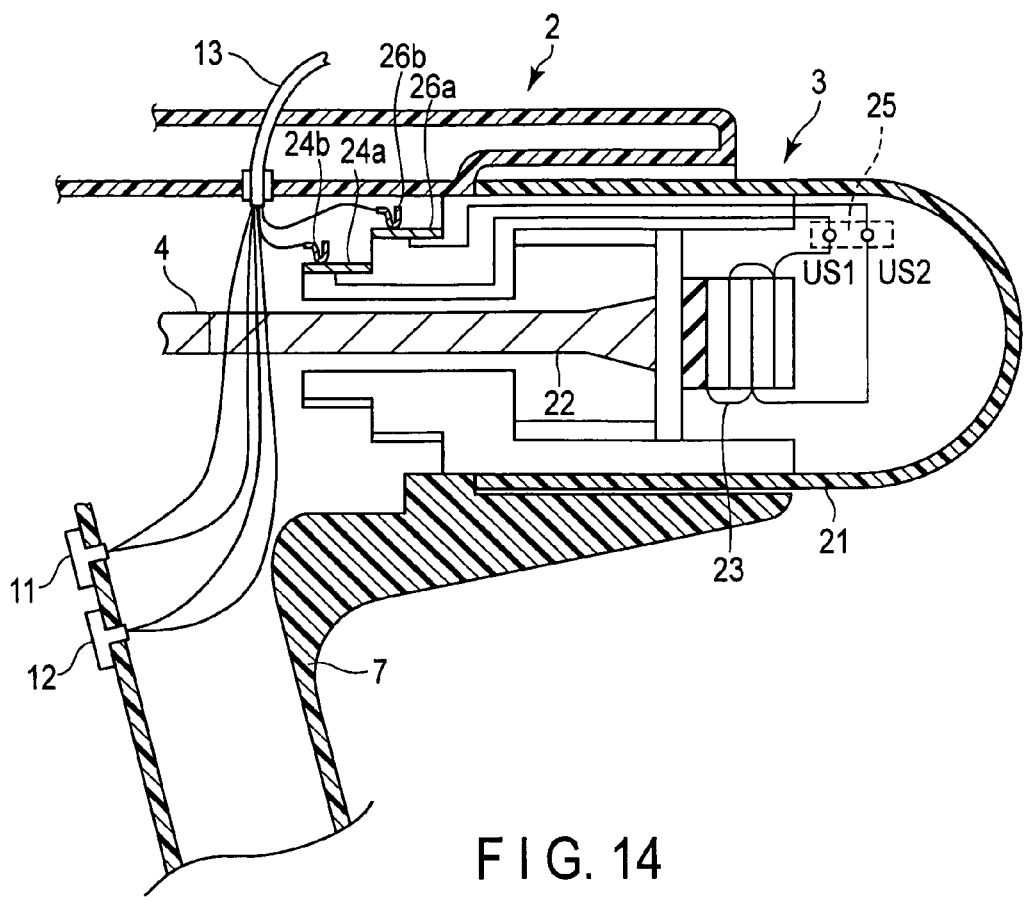
FIG. 14 is a cross-sectional view illustrating an internal structure example including a transducer unit according to a sixth embodiment.
Figure 15:
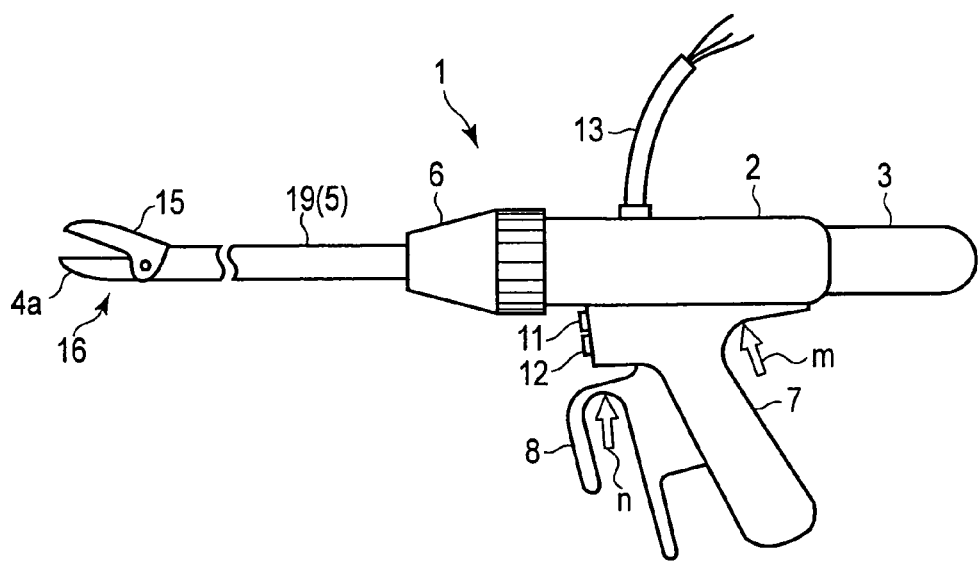
FIG. 15 is a view illustrating a lead-out position of a power cable which supplies power to an ultrasonic vibration element according to the sixth embodiment.

FIG. 14 is a cross-sectional view illustrating an internal structure example including a transducer unit according to the sixth embodiment. FIG. 15 is a view illustrating a lead-out position of a power cable which supplies power to an ultrasonic vibration element according to the sixth embodiment. In this embodiment, the same structural parts as in the above-described fourth embodiment are denoted by like reference numerals, and a detailed description thereof is omitted.

Incidentally, in this embodiment, any one of the rotatable structures of the cylindrical contact-point members and contact terminals for introducing a high-frequency signal for performing high-frequency treatment in the above-described first, second, third and fifth embodiments can be mounted. In the internal structure shown in FIG. 14, only the switch 12 is described, and the description of the other structure is omitted.

In the example of the above-described fourth embodiment, since the position of introduction of the power cable is disposed at the load force center of the treatment instrument or thereabout, the location of introduction of the power cable is disposed at the bottom part of the stationary handle 7. In the present invention, in the same manner, the position of introduction of the power cable is disposed at the load force center of the treatment instrument or thereabout.

As illustrated in FIG. 14, the present embodiment has a structure in which the position of introduction of the power cable 13 is disposed on the upper surface of the unit main body 21 (on the side opposite to the handle), at the position of the load force center of the handle unit 2 or thereabout.

The respective wires of the power cable 13, which is introduced from the upper surface side of the handle unit 2, are connected to the contact terminals 24b, 26b, and the ultrasonic application switch 11 and high-frequency application switch 12 above the movable handle 8. The contact terminals 24b, 26b are put in slidable contact with the cylindrical contact-point members 24a, 26a provided on the transducer unit 3. Accordingly, when the probe 4 rotates, the contact terminals 24b, 26b and cylindrical contact-point members 24a, 26a maintain the electrically connected state, and rotate while keeping supply of power to the ultrasonic vibration element 23. From the above, in the present embodiment, the same advantageous effects as in the above-described fourth embodiment can be obtained. Furthermore, at a time of an operation, when the wiring of the power cable is located below and interferes with other operation instruments or when it is difficult to secure a space under the handle unit 2, it is easy to operate the treatment instrument since the power cable is introduced from the upper side. Incidentally, in this embodiment, too, the position of introduction of the power cable is the position of the load force center of the treatment instrument or thereabout. In the case of such a shape that the treatment instrument is held at the two points, which are the thumb and another finger, at a time of performing treatment, the location of introduction of the power cable is disposed at a position between the two points, that is, at a balanced position between the two points, or near the load force center between the two points.

Seventh Embodiment

Next, a seventh embodiment is described.

Figure 16:
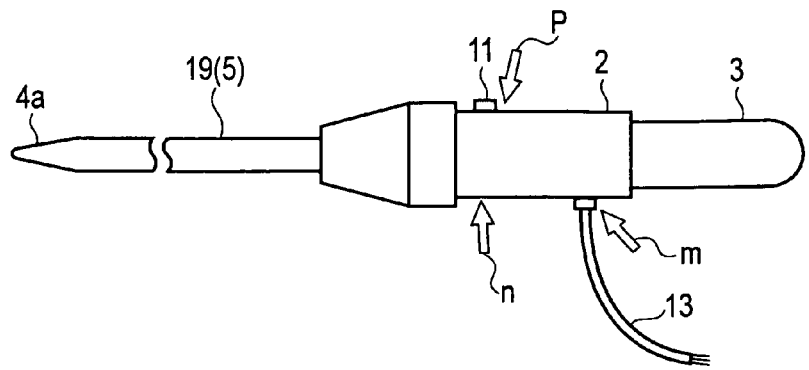
FIG. 16 is a view illustrating an example of the entire structure of a monopolar-type ultrasonic vibration treatment instrument according to a seventh embodiment.
Figure 17:
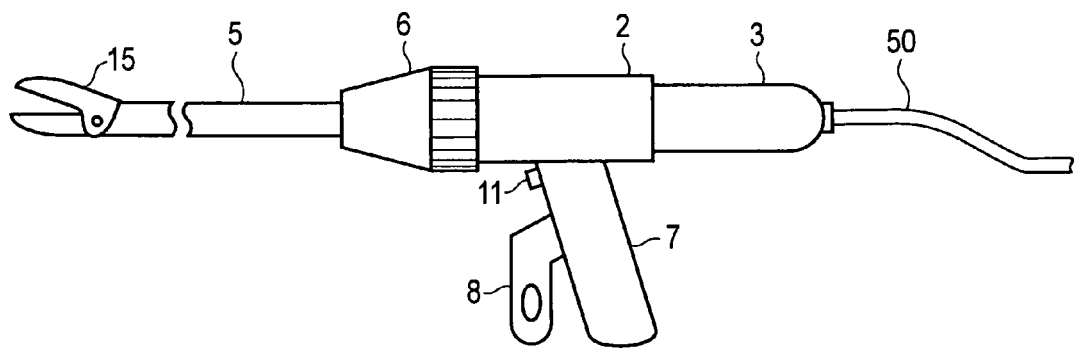
FIG. 17 is a view illustrating a lead-out position in the prior art of a power cable which supplies power to an ultrasonic vibration element.

FIG. 16 is a view illustrating a structure of the external appearance of the entirety of an ultrasonic vibration treatment instrument having a pen shape according to the present embodiment. In this embodiment, the structural parts having the same functions as the structural parts shown in the above-described FIG. 2 are denoted by like reference numerals, and a detailed description thereof is omitted.

FIG. 16 illustrates an ultrasonic vibration treatment instrument having a pen shape, which is a modification of the fourth embodiment. This treatment instrument has a pen shape, and is composed of a handle unit (treatment instrument main body) 2 which is disposable, and a transducer unit 3 which is repeatedly used by being subjected to sterilization treatment. In the treatment instrument, the transducer unit 3 outputs only ultrasonic vibrations, like the fourth embodiment.

The power unit, which supplies driving power to the piezoelectric element in the transducer unit 3, is the same as the above-described power unit 31.

In the handle unit 2, a probe unit 5, which penetrates and extends from the inside to outside and is formed of an elongated electrical conductor that propagates ultrasonic vibrations, is attached. The probe unit 5 includes a single tapered, rod-shaped probe 4 which is formed of an electrical conductor. The probe 4 is covered with a sheath unit 19.

A power cable 13 is disposed at a position where the power cable 13 does not become an obstacle at a time of holding the treatment instrument in such a manner that a pen is held by the hand, such that the location of introduction of the power cable 13 is disposed at the load force center of the treatment instrument, for example, between a base part m of the thumb and index finger and fingertips n, p thereof. An ultrasonic application switch 11 is disposed on an upper surface of the handle unit 2, and is ON/OFF operated by, for example, the fingertip of the index finger. Incidentally, if the structure for outputting a high-frequency signal is added, like the first embodiment, the use as a monopolar high-frequency treatment instrument is possible.

In this manner, by providing the position of introduction of the power cable 13 such that the hold position of the operator is disposed at the load force center of the treatment instrument, the entirety of the treatment instrument is balanced, and the operability is improved.

As has been described above, the treatment instrument of the present embodiment is configured to have the treatment capability by ultrasonic vibrations, or to have the treatment capability by high-frequency vibrations in addition to the treatment capability by ultrasonic vibrations. In addition, a slight movement of the distal end of the probe 5, which is caused by the cable, etc., is suppressed, the entire treatment instrument is balanced, and the operability is improved.

Since the position (load force center) at which a load acts in the treatment instrument lies between the two points which are the base part of the thumb of the hand and the fingertip of another finger, the load acts on the arm and the labor involved in the operation can be reduced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
a transducer unit that is configured to generate ultrasonic vibration, the transducer unit including:
an ultrasonic vibration element,
a case that stores the ultrasonic vibration element,
a contact-point member that is provided on an outer surface of the case, and
a first internal wiring that is configured to electrically connect the contact-point member and the ultrasonic vibration element, the first internal wiring being provided in the case; and
a handle unit that is configured to provide treatment to living tissue, the handle unit including:
a probe that is provided with a treatment section at a distal end of the probe and that is coupled to the ultrasonic vibration element at a proximal end of the probe, the treatment section being configured to treat living tissue and the probe extending in a longitudinal axis direction, a sheath unit that covers the probe, an engaging part that is provided in the handle unit and that is configured to rotatably hold the transducer unit in the longitudinal axis direction while coupling the ultrasonic vibration element and the probe when the transducer unit is attached to the handle unit, a contact member that is provided in the engaging part and that is provided at a position such that the contact member contacts the contact-point member when the transducer unit is attached to the handle unit, a second internal wiring that connects to the contact member at one end of the second internal wiring and that extends towards an outer surface of the handle unit at a second end of the second internal wiring, and a location of introduction of wires that is provided on the outer surface of the handle unit and that is configured to connect the second internal wiring and a power cable from an outside, wherein:

the contact-point member and the contact member form an electrically contact structure that constantly maintains a contact state by sliding together when the probe and the transducer unit are integrally rotated, and the second internal wiring, the contact member, the contact-point member, and the first internal wiring constitute a current path from the location of introduction to the ultrasonic vibration element.

2. The treatment instrument of claim 1, wherein the location of introduction includes a connector that is electrically connected to the second internal wiring and detachably holds the power cable.

3. The treatment instrument of claim 1, wherein:

the handle unit includes a fixed handle that is configured to be gripped by an operator, and the location of introduction is provided at a bottom section of the fixed handle.

4. The treatment instrument of claim 1, wherein the contact-point member is a cylindrical shaped contact-point member.

5. The treatment instrument of claim 1, wherein the contact-point member is a semi-circular contact-point member.

6. The treatment instrument of claim 1, wherein:

the probe transmits ultrasonic vibrations generated by the ultrasonic vibration element, and the probe includes a first high-frequency signal transmission path configured to transmit a high-frequency signal, and the power cable supplies either of a driving power and the high-frequency signal of the ultrasonic vibration element.

7. The treatment instrument of claim 6, wherein the sheath unit further includes:

a movable member that is configured to be moved in an axial direction of the probe and to function as a second high-frequency signal transmission path that is capable of transmitting a high-frequency signal;

a jaw that is provided at the distal end portion of the probe and that is configured to clamp a treatment target part and to rotate at an arbitrary angle; and an electrode section that is disposed on the jaw to provide treatment.

8. The treatment instrument of claim 1, further comprising:

a liquid-feed conduit that is provided in the treatment instrument for feeding a liquid to the distal end of the probe; and a suction conduit that is provided in the treatment instrument for sucking liquid existing in a vicinity of the distal end of the probe, wherein at least one of the liquid-feed conduit and the suction conduit are provided to pass through a position of introduction.

9. The treatment instrument of claim 1, further comprising:

a rotational knob that is provided in the treatment instrument for integrally rotating the probe and the transducer unit relative to the handle unit around the longitudinal axis of the probe, wherein the electrically contact structure constantly maintains a contact state by sliding together when the probe and the transducer unit are integrally rotated by the rotational knob.

10. An ultrasonic treatment system comprising:

a treatment instrument;

an outer power source; and a power cable, wherein:

the treatment instrument includes:

a transducer unit that is configured to generate ultrasonic vibration, the transducer unit including:

an ultrasonic vibration element, a case that stores the ultrasonic vibration element, a contact-point member that is provided on an outer surface of the case, and a first internal wiring that is configured to electrically connect the contact-point member and the ultrasonic vibration element, the first internal wiring being provided in the case; and a handle unit that is configured to provide treatment to living tissue, the handle unit including:

a probe that is provided with a treatment section at a distal end of the probe and that is coupled to the ultrasonic vibration element at a proximal end of the probe, the treatment section being configured to treat living tissue and the probe extending in a longitudinal axis direction, a sheath unit that covers the probe, an engaging part that is provided in the handle unit and that is configured to rotatably hold the transducer unit in the longitudinal axis direction while connecting the ultrasonic vibration element and the probe when the transducer unit is attached to the handle unit, a contact member that is provided in the engaging part and that is provided at a position such that the contact member contacts the contact-point member when the transducer unit is attached to the handle unit, and a location of introduction of wires that is provided on the outer surface of the handle unit;

the outer power source is configured to supply driving current to the power cable, the power cable is configured to connect to the contact member through a second internal wiring at one end of the power cable and to connect to the outer power source at the other end of the power cable to transmit driving current by being inserted into the location of introduction, the contact point member and the contact member form an electrically contact structure that constantly maintains a contact state by sliding together when the probe and the transducer unit are integrally rotated, and the driving current supplied from the outer power source flows to the ultrasonic vibration element via the power cable, the contact member, the contact-point member, and the first internal wiring.

* * * * *

UNITED STATES PATENT AND TRADEMARK OFFICE
CERTIFICATE OF CORRECTION

PATENT NO. : 9,492,688 B2
APPLICATION NO. : 14/470055
DATED : November 15, 2016
INVENTOR(S) : Hideo Sanai et al.

It is certified that error appears in the above-identified patent and that said Letters Patent is hereby corrected as shown below:

On the Title Page

(54) and in the Specification, Column 1, Lines 1 and 2: please amend the title as follows:

TREATMENT INSTRUMENT USING ULTRASONIC VIBRATIONS

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*